(12) United States Patent
Tamura

(10) Patent No.: US 12,274,570 B2
(45) Date of Patent: Apr. 15, 2025

(54) RADIATION IMAGING SYSTEM, IMAGING CONTROL APPARATUS, RADIATION IMAGING APPARATUS, RADIATION IMAGING METHOD, AND NON-TRANSITORY COMPUTER READABLE STORAGE MEDIUM

(71) Applicant: CANON KABUSHIKI KAISHA, Tokyo (JP)

(72) Inventor: Toshikazu Tamura, Tochigi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 151 days.

(21) Appl. No.: 17/977,270

(22) Filed: Oct. 31, 2022

(65) Prior Publication Data

US 2023/0049588 A1 Feb. 16, 2023

Related U.S. Application Data

(63) Continuation of application No. PCT/JP2021/017263, filed on Apr. 30, 2021.

(30) Foreign Application Priority Data

May 15, 2020 (JP) .................. 2020-086046

(51) Int. Cl.
*A61B 6/42* (2024.01)
*A61B 6/46* (2024.01)

(52) U.S. Cl.
CPC ............ *A61B 6/4208* (2013.01); *A61B 6/461* (2013.01)

(58) Field of Classification Search
CPC .............................. A61B 6/4208; A61B 6/461
See application file for complete search history.

(56) References Cited

U.S. PATENT DOCUMENTS

| 10,288,747 B2 | 5/2019 | Tamura et al. |
| 10,585,196 B2 | 3/2020 | Tamura et al. |

(Continued)

FOREIGN PATENT DOCUMENTS

| JP | 2014158580 A | 9/2014 |
| JP | 2016139619 A | 8/2016 |

(Continued)

OTHER PUBLICATIONS

International Search Report issued by the Japan Patent Office on Jun. 22, 2021 in corresponding International Application No. PCT/JP2021/017263, with English translation.

(Continued)

*Primary Examiner* — Hugh Maupin
(74) *Attorney, Agent, or Firm* — Carter, DeLuca & Farrell LLP

(57) ABSTRACT

A radiation imaging system includes a radiation imaging apparatus and an imaging control apparatus, the radiation imaging apparatus includes a dose detection pixel that detects a dose of radiation irradiated from a radiation source, and the imaging control apparatus controls the radiation imaging apparatus. Before radiation imaging, the imaging control apparatus specifies a position of the dose detection pixel in a region of interest for calculating a dose indicator value of a radiation image, determines a threshold according to the position of the dose detection pixel, and transmits the position of the dose detection pixel and the threshold to the radiation imaging apparatus. The radiation imaging apparatus makes a setting of the position of the dose detection pixel in the region of interest and the threshold transmitted from the imaging control apparatus, and performs imaging based on the setting.

20 Claims, 13 Drawing Sheets

(56) References Cited

U.S. PATENT DOCUMENTS

| | | | |
|---|---|---|---|
| 2011/0249791 A1 | 10/2011 | Wang | |
| 2012/0318986 A1* | 12/2012 | Kanagawa | H04N 5/32 250/354.1 |
| 2013/0208852 A1* | 8/2013 | Koishi | A61B 6/5288 378/19 |
| 2014/0205066 A1* | 7/2014 | Kitagawa | H04N 5/32 378/62 |
| 2015/0182182 A1 | 7/2015 | Tajima | |
| 2019/0054320 A1* | 2/2019 | Owens | A61B 6/032 |
| 2022/0361830 A1* | 11/2022 | Loustauneau | A61B 6/469 |

FOREIGN PATENT DOCUMENTS

| | | |
|---|---|---|
| JP | 2017148310 A | 8/2017 |
| JP | 2020025730 A | 2/2020 |
| WO | 2013047170 A1 | 4/2013 |
| WO | 2014045835 A1 | 3/2014 |
| WO | 2017187776 A1 | 11/2017 |

OTHER PUBLICATIONS

Extended European Search Report issued in EP Patent Application No. 21804248.9, dated Mar. 21, 2024, pp. 1-6.
Notice of Reasons for Refusal issued by the Japanese Patent Office on May 17, 2024 in corresponding JP Patent Application No. 2020-086046, with English translation.

* cited by examiner

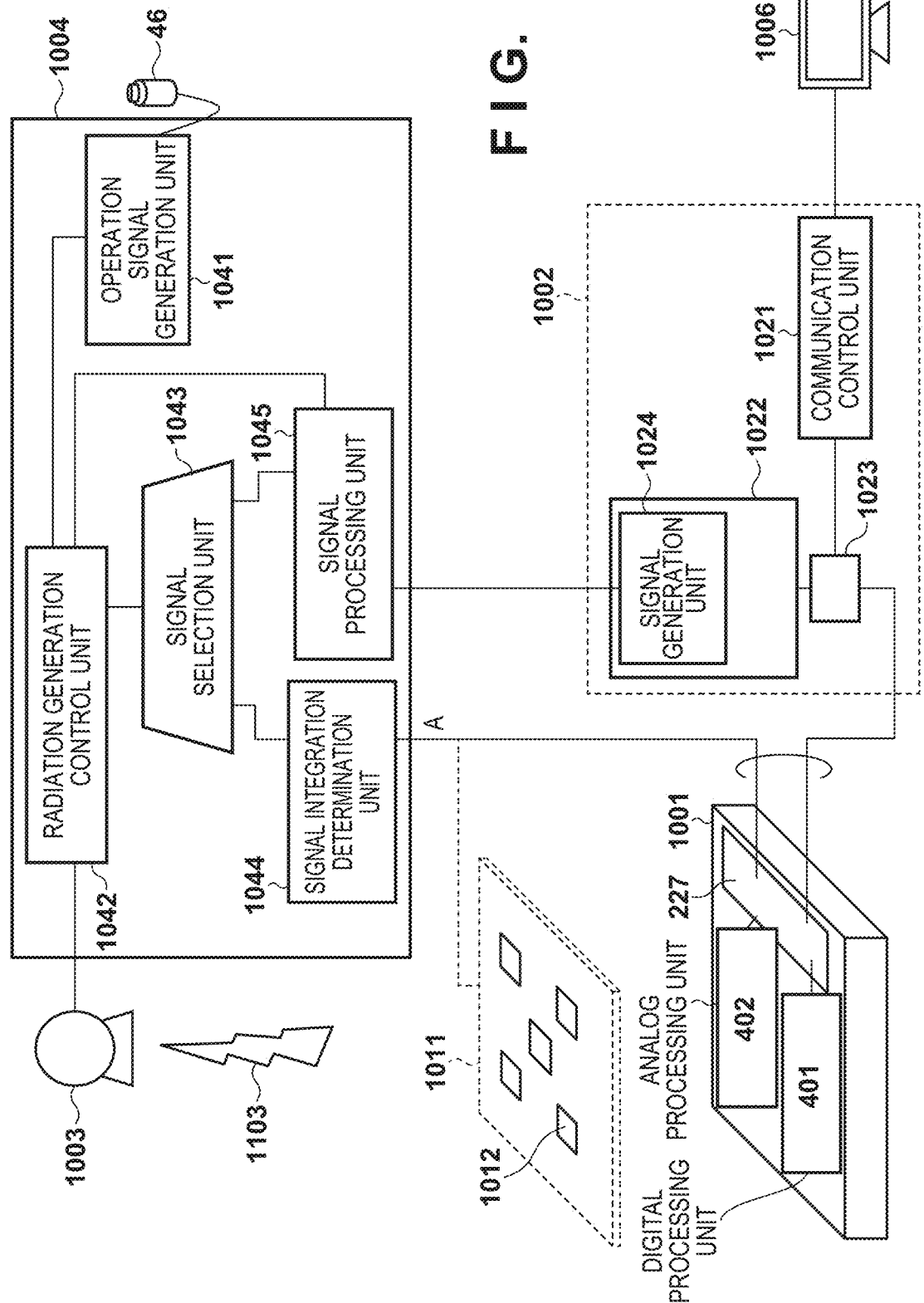

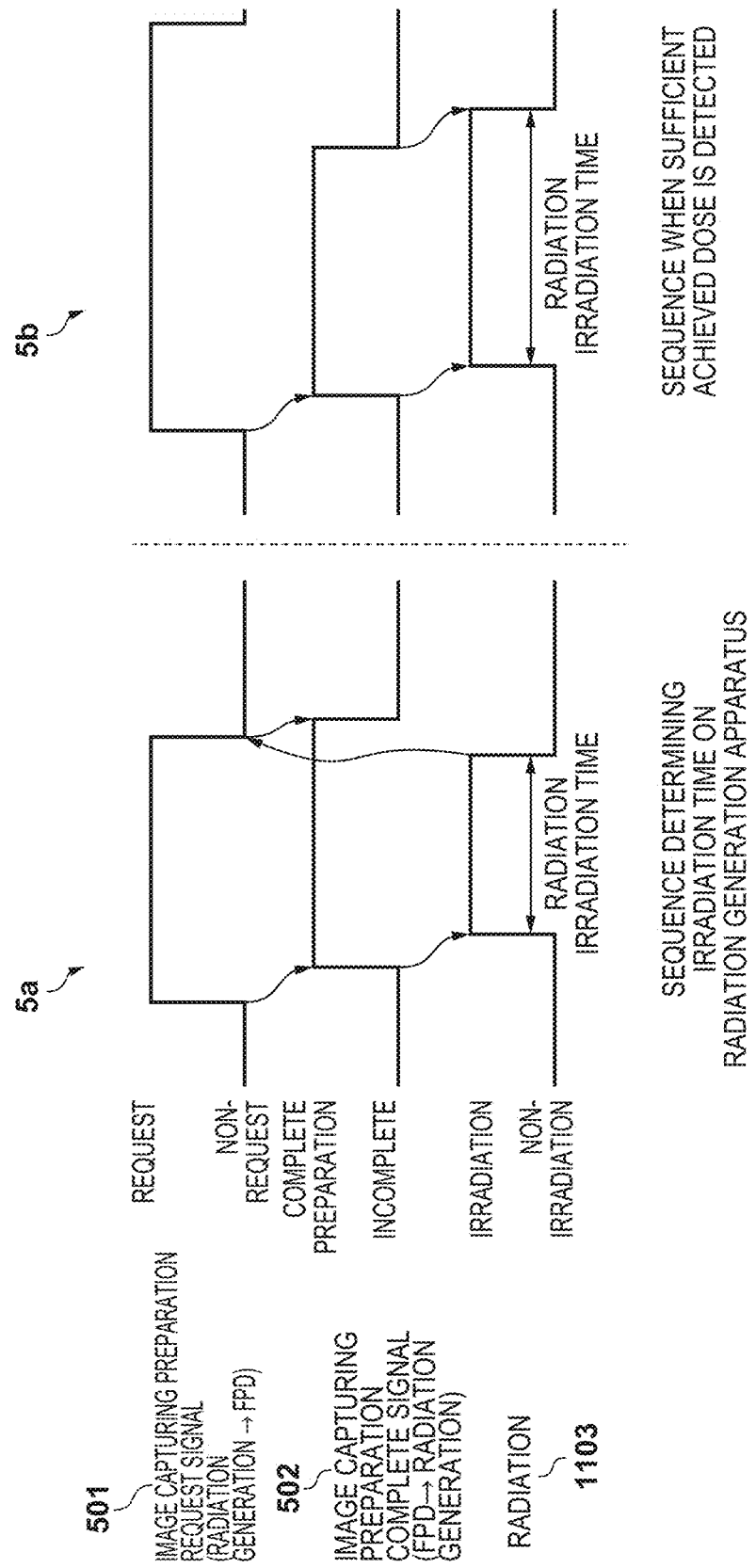

RADIATION IMAGING SYSTEM, IMAGING CONTROL APPARATUS, RADIATION IMAGING APPARATUS, RADIATION IMAGING METHOD, AND NON-TRANSITORY COMPUTER READABLE STORAGE MEDIUM

CROSS-REFERENCE TO RELATED APPLICATIONS

This application is a Continuation of International Patent Application No. PCT/JP2021/017263, filed Apr. 30, 2021, which claims the benefit of Japanese Patent Application No. 2020-086046, filed May 15, 2020, both of which are hereby incorporated by reference herein in their entirety.

BACKGROUND OF THE INVENTION

Field of the Invention

The present invention relates to a radiation imaging system, an imaging control apparatus, a radiation imaging apparatus, a radiation imaging method, and a non-transitory computer readable storage medium.

Background Art

Radiation imaging apparatuses which use radiation such as X-rays for medical image diagnoses, non-destructive testing, and the like have matrix substrates which include pixel arrays that combine switches such as thin-film transistors (TFTs) with conversion elements such as photoelectric conversion elements.

This radiation imaging apparatus has an extremely wide dynamic range with respect to the radiation dose, and, by performing automatic density correction through image processing, has the advantage of providing output at a more stable density than conventional analog radiation imaging, even in conditions where the dose is insufficient or excessive. However, there is a problem in that it is difficult for the technician to notice when they capture an image at an insufficient dose, which increases the amount of radiation to which the patient is exposed, especially at excessive doses.

Accordingly, to solve this problem, it is common practice to display a value that serves as a guideline for the imaging dose in a digital radiation image (called a "dose indicator value" hereinafter) along with the captured image. A variety of methods for calculating the dose indicator value have been proposed. The International Electrotechnical Commission (IEC) recently issued the international standard IEC62494-1, which defines an "Exposure Index (EI)" as a standardized dose indicator value. In this international standard, EIt (Target Exposure Index) is specified as the value of the dose to serve as a target (called "dose target value" hereinafter), and an operational method is also given for managing the dose using a deviation DI (Deviation Index), which represents the amount of deviation between the dose indicator value EI and the dose target value EIt.

Japanese Patent Laid-Open No. 2014-158580 describes an apparatus having an AEC function that stops X-ray irradiation at a target dose, in which a receptor field, which is a region of detection pixels which detect the dose, is automatically set during X-ray irradiation based on pixel values of the detection pixels, and the dose indicator value EI is calculated based on a representative value V extracted from the pixel values in the receptor field.

Japanese Patent Laid-Open No. 2020-025730 describes dividing a radiation image into a plurality of anatomical regions, extracting at least one of the plurality of anatomical regions, and calculating the dose indicator value EI of the radiation imaging for the extracted region based on pixel values in the extracted region.

In managing doses in radiation imaging, there is a need for the amount of deviation between the dose indicator value EI and the dose target value EIt to be low.

Accordingly, the present invention provides a radiation imaging technique which enables appropriate dose management by reducing deviation between a dose target value set as a radiation irradiation threshold and a dose indicator value from when an image is actually taken.

SUMMARY OF THE INVENTION

According to one aspect of the present invention, there is provided a radiation imaging system comprising a radiation imaging apparatus and an imaging control apparatus, the radiation imaging apparatus including a dose detection pixel that detects a dose of radiation irradiated from a radiation source, and the imaging control apparatus controlling the radiation imaging apparatus, wherein before radiation imaging, the imaging control apparatus:
  specifies a position of the dose detection pixel in a region of interest for calculating a dose indicator value of a radiation image, determines a threshold according to the position of the dose detection pixel, and transmits the position of the dose detection pixel and the threshold to the radiation imaging apparatus, and
  the radiation imaging apparatus:
  makes a setting of the position of the dose detection pixel in the region of interest and the threshold transmitted from the imaging control apparatus, and performs imaging based on the setting.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the present invention and, together with the description, serve to explain principles of the present invention.

FIG. 4 is a diagram illustrating the functional configuration of the radiation imaging system in an embodiment.

FIG. 5 is a diagram illustrating an example of operations of the radiation imaging system based on digital signals.

DESCRIPTION OF THE EMBODIMENTS

Figure 1:
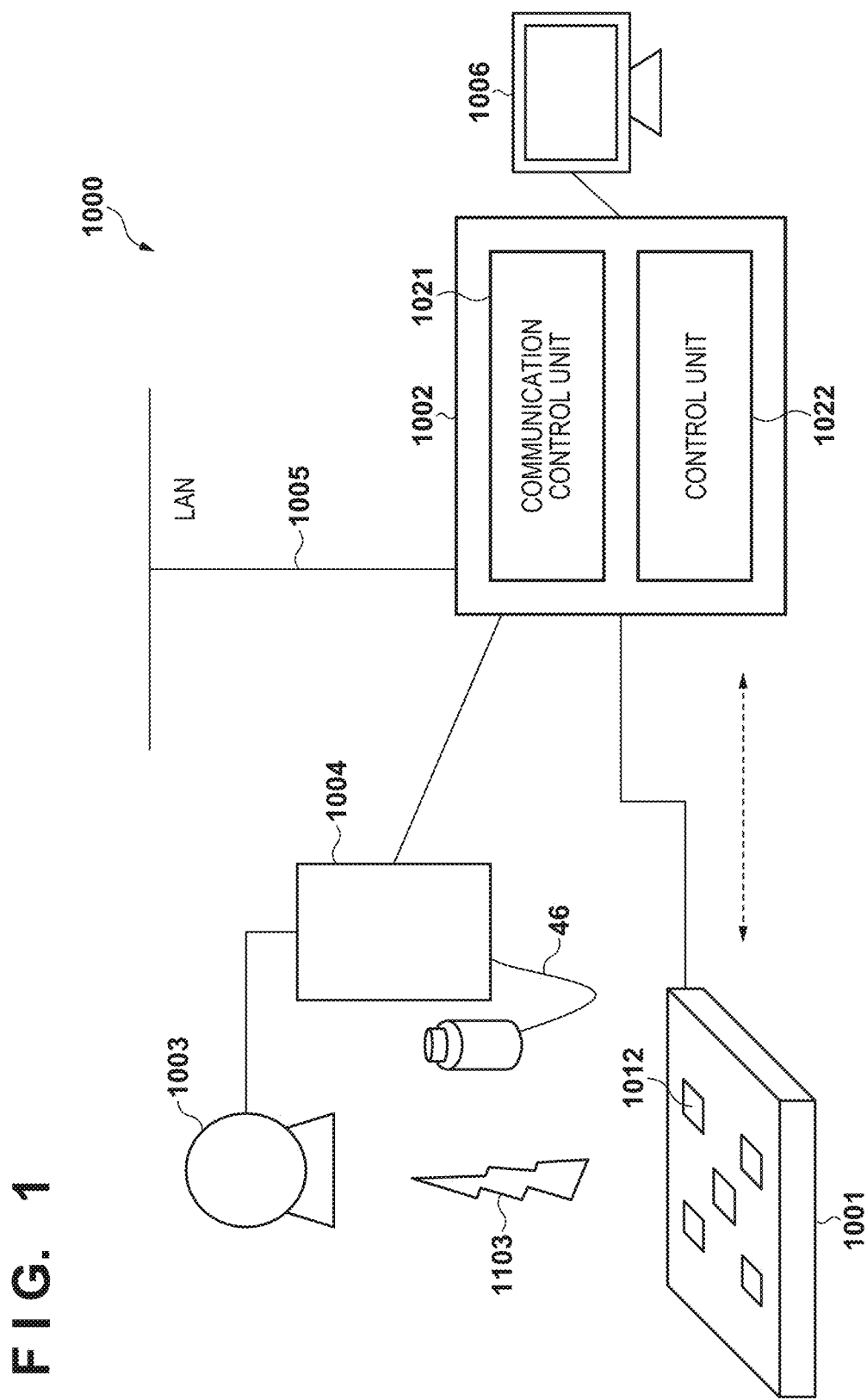
FIG. 1 is a diagram illustrating an example of the configuration of a radiation imaging system including a radiation imaging apparatus.

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted. In the embodiments and the scope of patent claims described hereinafter, "radiation" includes α rays, β rays, γ rays, various particle rays, and the like in addition to X-rays.
Configuration of Radiation Imaging System The configuration of, and processing by, a radiation imaging system 1000 according to the present embodiment will be described hereinafter with reference to FIG. 1. FIG. 1 is a block diagram illustrating an example of the configuration of a radiation imaging system including a radiation imaging apparatus according to the present embodiment. The radiation imaging system 1000 is used, for example, when shooting a radiation image in a hospital, and includes, as a system configuration, a radiation imaging apparatus 1001, an imaging control apparatus 1002, a radiation source 1003, a high-voltage generation apparatus 1004, a LAN 1005 (an in-hospital LAN), and a display unit 1006.

The radiation imaging apparatus 1001 detects radiation passing through an object (not shown) and forms an image in response to an operator operating an operation switch 46. The imaging control apparatus 1002 makes shooting condition settings, operation control settings, and the like, for example, in the radiation imaging apparatus 1001, and the radiation imaging apparatus 1001 performs communication with the imaging control apparatus 1002 such as, for example, transferring images, transmitting the achieved dose, communicating automatic exposure control signals for controlling irradiation from the radiation source 1003, and the like.

The imaging control apparatus 1002 includes, for example, a mouse and keyboard as input devices to enable input of information such as setting shooting conditions, operation settings, and image information, and a display or the like as an output device to enable output. The imaging control apparatus 1002 also controls the irradiation of radiation with respect to the high-voltage generation apparatus 1004. The imaging control apparatus 1002 has, as a functional configuration, a communication control unit 1021 that performs and mediates communication and a control unit 1022 that makes operation settings, dose information notifications, and the like, and monitors the status of the radiation imaging apparatus 1001 and the high-voltage generation apparatus 1004 to control the irradiation of radiation and image capturing. It is also possible to provide the communication control unit 1021 as a separate unit of the imaging control apparatus 1002 and have the communication control unit 1021 operate as a circuit for mediating communication of the imaging control apparatus 1002.

The radiation source 1003 includes, for example, an X-ray tube and a rotor that accelerate electrons with high voltage to generate radiation and cause the electrodes to impinge upon an anode. The object is irradiated with the radiation emitted from the radiation source 1003, and the radiation imaging apparatus 1001 detects the radiation passing through the object and forms an image. For convenience, FIG. 1 illustrates the imaging control apparatus 1002 and the high-voltage generation apparatus 1004 as being disposed in separate locations, but the imaging control apparatus 1002 and the high-voltage generation apparatus 1004 may be disposed in the same unit. Functions other than the image capturing function may be provided in any part other than the radiation imaging apparatus 1001.

Figure 2:
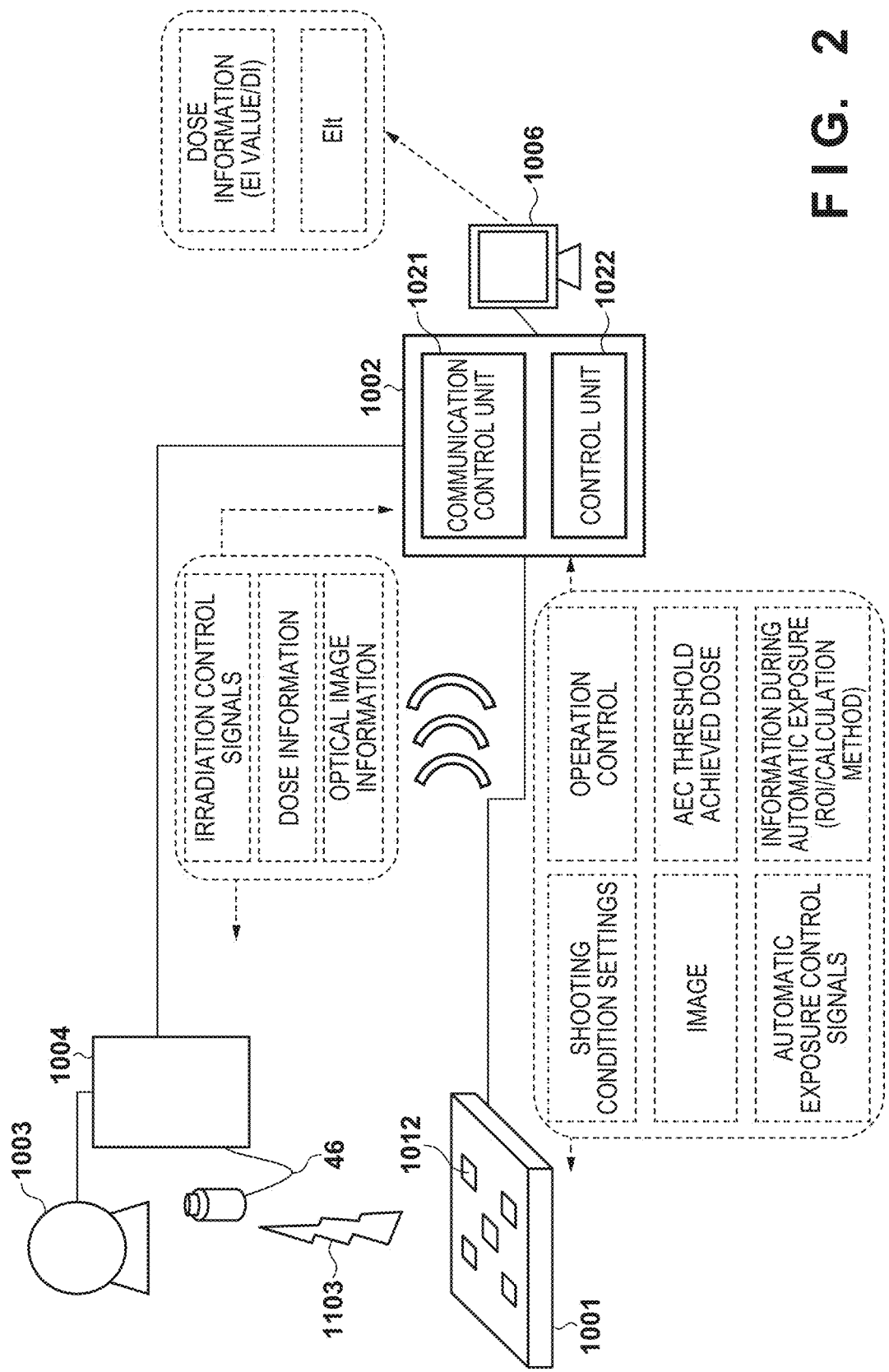
FIG. 2 is a diagram illustrating an example of data communication in the radiation imaging system.

FIG. 2 is a diagram illustrating an example of data communication in the radiation imaging system. FIG. 2 illustrates an example of data communication between the imaging control apparatus 1002, the radiation imaging apparatus 1001, and the high-voltage generation apparatus 1004. In the communication between the imaging control apparatus 1002 and the radiation imaging apparatus 1001, information such as the shooting condition settings, operation control settings, image transfer, AEC threshold, achieved dose, automatic exposure control signals, information during automatic exposure, and the like is transmitted and received. The radiation imaging apparatus 1001 has two communication units, namely a wireless communication unit and a wired communication unit, and the radiation imaging apparatus 1001 can be connected to the communication control unit 1021 of the imaging control apparatus 1002 using the two communication units.

Information such as dose information, irradiation control signals, optical image information using visible light, infrared light, and the like related to a planned irradiation area are transmitted and received in the communication between the imaging control apparatus 1002 and the high-voltage generation apparatus 1004. This optical image information is information, pertaining to what is optically the same focus, aperture, and the like as the radiation, which can be shared between the imaging control apparatus 1002 and the high-voltage generation apparatus 1004.

The transmission path for communicating information does not necessarily need to be mediated by the imaging control apparatus 1002, and data may be transmitted and received directly through communication between the radiation imaging apparatus 1001 and the high-voltage generation apparatus 1004, or the information may be shared among the imaging control apparatus 1002, the radiation imaging apparatus 1001, and the high-voltage generation apparatus 1004 through communication based on a data transfer standard such as Controller Area Network (CAN).

"Dose information" refers to the dose of radiation irradiated from the radiation source 1003, and "achieved dose" refers to the dose that reaches the radiation imaging apparatus 1001 among the dose irradiated from the radiation source 1003.

The "AEC threshold" is threshold information which is set as the dose target value and serves as a reference for comparison with the achieved dose. This "AEC threshold" corresponds to the dose information per unit of area. The "AEC threshold" is set to reflect the dose target value EIt, which is set in advance. The imaging control apparatus 1002 compares the "AEC threshold" with the achieved dose calculated within the radiation imaging apparatus 1001, and at the timing when the AEC threshold exceeds the achieved dose, notifies the high-voltage generation apparatus 1004 thereof. The imaging control apparatus 1002 converts this into the dose information per unit of area as appropriate, and performs processing for comparing the AEC threshold with the achieved dose.

The "automatic exposure control signal" is a signal that includes two signals, which are, for example, a stop signal for stopping the irradiation of radiation (an irradiation stop signal) and an irradiation start signal for starting the irradiation of radiation (a non-irradiation stop signal).

The "information during automatic exposure (ROI/calculation method)" is instruction information indicating a region of interest ROI (receptor field) for automatic exposure control, a calculation method, and the like transmitted to the radiation imaging apparatus 1001 from the imaging control apparatus 1002. The ROI (receptor field 1012), information corresponding to the calculation method, and the like from when automatic exposure is actually performed are transmitted to the imaging control apparatus 1002 from the radiation imaging apparatus 1001.

Additionally, the imaging control apparatus 1002 controls the display of the display unit 1006 to display "dose information (dose indicator value EI/deviation DI)" during image capturing, display the input of settings for the "dose target value EIt", or display control for displaying information set during radiation imaging.

The wired communication unit, which is included in the radiation imaging apparatus 1001 as a communication medium, is a path for transmitting information, and enables the transmission and reception of information through a cable connection using, for example, a communication standard having predetermined arrangements, or a standard such as RS232C, USB, Ethernet (registered trademark), or the like. Additionally, the wireless communication unit, which is included in the radiation imaging apparatus 1001 as a communication medium, is similarly a path for transmitting information, and includes, for example, a circuit board having a communication IC and the like. The wireless communication unit is electrically connected to an antenna (not shown), and wirelessly transmits and receives radio waves. The circuit board having a communication IC and the like can perform communication processing according to a protocol based on wireless LAN through the antenna. The frequency band, standard, method, and the like of the wireless communication are not particularly limited, and short-range wireless such as Near Field Radio Communication (NFC) and Bluetooth (registered trademark), Ultra Wideband (UWB), or the like may be used. Additionally, the wireless communication unit may have a plurality of wireless communication methods, which may be selected for communication as appropriate.

Figure 3:
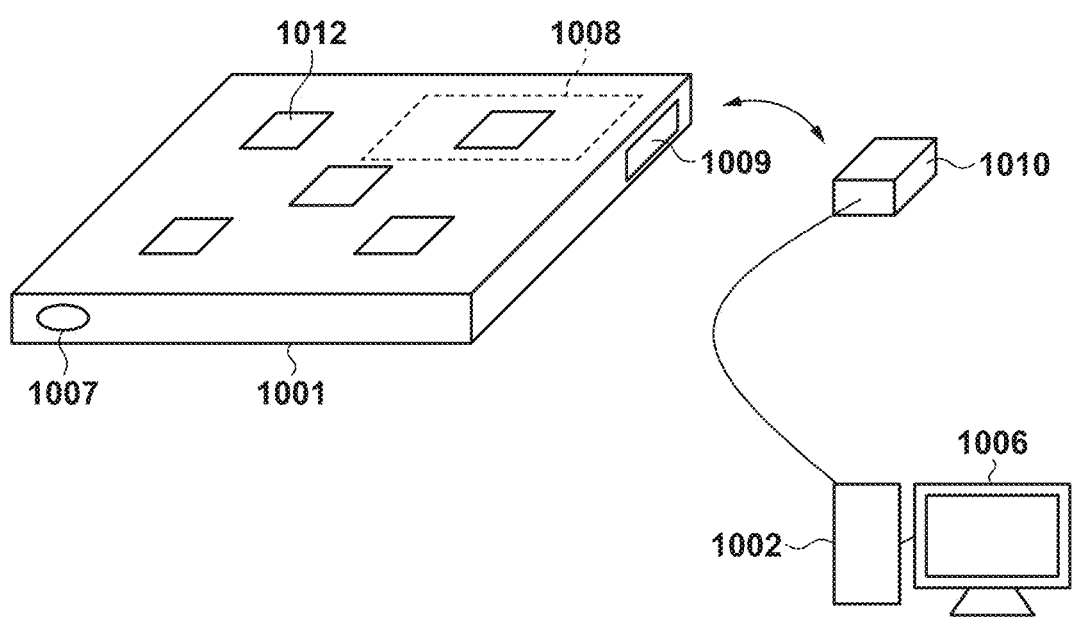
FIG. 3 is a diagram illustrating an example of the external configuration of the radiation imaging apparatus.

The radiation imaging apparatus 1001 can be configured as a portable cassette-type flat-panel detector (FPD), for example. FIG. 3 is a diagram illustrating an example of the external configuration of the portable radiation imaging apparatus 1001. The radiation imaging apparatus 1001 includes a power button 1007 for turning the power on and off, a battery unit 1008 for supplying power, and a connector connection unit 1009. The battery unit 1008 is configured to be removable, and the battery body of the battery unit 1008 is configured to be rechargeable by a battery charger.

The radiation imaging apparatus 1001 can be connected to the imaging control apparatus 1002 using a sensor cable 1010, and the radiation imaging apparatus 1001 connects the sensor cable 1010 through the connector connection unit 1009. When the radiation imaging apparatus 1001 and the imaging control apparatus 1002 are connected by the sensor cable 1010, the connection between the two switches to communication using the wired communication unit, and the information communication between the radiation imaging apparatus 1001 and the imaging control apparatus 1002 illustrated in FIG. 2 is executed through wired communication. The communication unit may be switchable by the imaging control apparatus 1002 in response to operations by a user regardless of the connection format.

The functional configuration of the radiation imaging system 1000 of the present embodiment will be described with reference to FIG. 4. A signal from the radiation source 1003, and a signal from an operation signal generation unit 1041, are input into a radiation generation control unit 1042 of the high-voltage generation apparatus 1004. A signal expressing a stable state of anode rotation, a signal expressing a temperature state, and the like are input to the radiation generation control unit 1042 from the radiation source 1003. The operation switch 46 is connected to the operation signal generation unit 1041, and an input signal from a switch operation made by an operator is input to the radiation generation control unit 1042.

Additionally, various signals are input to the radiation generation control unit 1042 from the radiation imaging apparatus 1001 and the imaging control apparatus 1002, via a signal selection unit 1043, a signal integration determination unit 1044, and a signal processing unit 1045. A signal expressing a shooting preparation state is input to the radiation generation control unit 1042 from the radiation imaging apparatus 1001. A signal pertaining to exposure control (described later) is input to the radiation generation control unit 1042 through the signal selection unit 1043. The stop signal for radiation 1103 in an analog signal path from the signal integration determination unit 1044, and the stop signal for the radiation 1103 in a digital communication path from the signal processing unit 1045, are input to the signal selection unit 1043, and the signal which was input first is transmitted to the radiation generation control unit 1042.

The radiation imaging apparatus 1001 of the present embodiment includes a digital processing unit 401 that outputs the stop signal when dose information obtained based on first processing (digital signal processing) performed on a result of detection by a dose detection pixel (a detection unit) exceeds a threshold, and an analog processing unit 402 (conversion processing unit) that outputs a signal obtained by performing second processing (analog conversion processing) on the signal subjected to the first processing (digital signal processing) by the digital processing unit 401.

The digital processing unit 401 (a first processing unit) generates a signal obtained by subjecting the detection result from the dose detection pixel to digital signal processing as the first processing. The digital processing unit 401 (the first processing unit) is capable of outputting the generated signal as a synchronization control signal with the radiation source 1003. The digital processing unit 401 (the first processing unit) is configured to, for example, detect the irradiation of radiation on the radiation imaging apparatus 1001, compute the irradiated dose of radiation and an integrated irradiation amount (integrated dose), and the like based on the generated signal. The digital processing unit 401 (the first processing unit) outputs a stop signal (a first stop signal) when the obtained dose information exceeds the threshold based on the first processing (the digital signal processing) on the result of detection by a dose detection pixel 121 (the detection unit).

The analog processing unit 402 (the conversion processing unit) and the signal integration determination unit 1044 (an integration determination unit) constitute a second processing unit in the radiation imaging system 1000 of the present embodiment. The second processing unit outputs a stop signal (a second stop signal) when the obtained dose information exceeds the threshold based on the second processing (the analog conversion processing) on the signal subjected to the first processing (the digital signal processing) by the digital processing unit 401 (the first processing unit).

Here, the analog processing unit 402 (the conversion processing unit) outputs the signal obtained by performing the second processing (the analog conversion processing) on the signal subjected to the first processing (the digital signal processing) by the digital processing unit 401 (the first processing unit), and the signal integration determination unit 1044 determines whether the dose information, obtained by performing integration processing on the signal output from the analog processing unit 402 (the conversion processing unit), exceeds the threshold. The second processing unit outputs the stop signal (the second stop signal) when the signal integration determination unit 1044 (the integration determination unit) determines that the dose information exceeds the threshold.

The radiation generation control unit 1042 controls the radiation source 1003 based on the first stop signal output from the digital processing unit 401 (the first processing unit) or the second stop signal output from the analog processing unit 402 and the signal integration determination unit 1044 (the second processing unit). In other words, the radiation generation control unit 1042 controls the radiation source 1003 to stop the irradiation of radiation based on the first stop signal or the second stop signal.

The stop signal (the second stop signal) for the radiation 1103 input through the analog signal path (a second signal path) from the signal integration determination unit 1044 (the integration determination unit), and the stop signal (the first stop signal) for the radiation 1103 input through the digital signal path (a first signal path) from the signal processing unit 1045, are input to the signal selection unit 1043 (a selection unit). The stop signal input first is selected by the signal selection unit 1043 (the selection unit), and the selected stop signal is transmitted to the radiation generation control unit 1042. In other words, the signal selection unit 1043 (the selection unit) selects the input first stop signal or second stop signal. At this time, the signal selection unit 1043 (the selection unit) selects the signal, of the first stop signal and the second stop signal, that was input to the signal selection unit 1043 (the selection unit) first.

The radiation generation control unit 1042 controls the generation of radiation while confirming the states of each input. The radiation generation control unit 1042 controls the irradiation of radiation from the radiation source 1003 based on a signal pertaining to the exposure state, which has been input. In other words, the radiation generation control unit 1042 controls the radiation source 1003 to stop the irradiation of radiation based on the signal selected by the signal selection unit 1043 (the selection unit).

Additionally, the radiation imaging apparatus 1001 can communicate with the signal processing unit 1045 of the high-voltage generation apparatus 1004 via a relay unit 1023 and a signal generation unit 1024 of the imaging control apparatus 1002. A signal expressing an image capture preparation state is input to the signal processing unit 1045 from the radiation imaging apparatus 1001 via the relay unit 1023 and the signal generation unit 1024 of the imaging control apparatus 1002. The signal processing unit 1045 inputs, to the radiation generation control unit 1042, the input signal expressing the image capture preparation state. Here, when the communication between the radiation imaging apparatus 1001 and the imaging control apparatus 1002 is wireless communication, the relay unit 1023 functions as an access point, whereas when the communication is wired communication, the relay unit 1023 functions as a switching hub. The communication control unit 1021 is further connected to the relay unit 1023, and the functions of the communication control unit 1021 are realized by application software running on a platform such as a PC (an information processing apparatus).

In the present embodiment, there are signal paths for two types of dose control using analog signals and digital signals. One of the signal paths is a signal path of analog signals for dose control (the second signal path), and is connected from a communication unit 227 of the radiation imaging apparatus 1001 to the signal integration determination unit 1044 in the high-voltage generation apparatus 1004. This analog signal is an output signal that simulates the output of a dose control sensor 1011 (an analog output signal for dose control). This connection format makes it possible to use the processing circuitry of the high-voltage generation apparatus 1004 to process the analog output signal from the dose control sensor 1011, and is therefore a connection format which does not require any changes to the processing circuitry of the high-voltage generation apparatus 1004. Note that the dose control sensor 1011 is a dose control sensor of the ion chamber type, a type that applies phosphor to an optical fiber and detects the phosphor with an image intensifier, a type that uses a thin-film semiconductor sensor, or the like. As will be described later, this signal path is configured such that a circuit configuration for dose control is provided in the high-voltage generation apparatus 1004. Note that the dose control can be configured redundantly using the dose control sensor 1011, using the output also as an analog signal, instead of using the radiation imaging apparatus 1001.

As illustrated in FIG. 4, five receptor fields 1012 are set in the dose control sensor 1011. Note that the setting of the receptor fields 1012 is merely an example, and the spirit of the embodiment is not intended to be limited to this example. In the example illustrated in FIG. 4, the receptor fields 1012, which are based on five areas, correspond to respective ones of a plurality of dose detection pixels 121 of the radiation imaging apparatus 1001. The operator can select the receptor fields 1012 from set irradiation area patterns using a user interface (a setting unit; not shown) in the high-voltage generation apparatus 1004. Based on the operation input by the operator, the user interface (setting unit) sets the irradiation area of the radiation source. Once the irradiation area of the radiation source is set, a control circuit 225 of the radiation imaging apparatus 1001 (FIGS. 6A to 6C) can specify the dose detection pixels 121 (detection units) arranged in positions corresponding to the set irradiation area from among the plurality of dose detection pixels 121 (detection units) arranged in an image capturing region 100. Additionally, the control unit 1022 of the imaging control apparatus 1002 (an obtainment unit) can obtain information on an image capturing site of an object from information from an image capture order system such as a Hospital Information System (HIS) or a Radiology Information System (RIS) over the LAN 1005. When information on the image capturing site of the object is obtained by the control unit 1022 (the obtainment unit), the control circuit 225 (a specifying unit) of the radiation imaging apparatus 1001 can specify the dose detection pixels 121 (detection units), among the plurality of dose detection pixels 121 (detection units) arranged in the image capturing region 100, that are arranged in positions corresponding to the image capturing site of the object.

The digital processing unit 401 (the first processing unit) of the radiation imaging apparatus 1001 obtains the dose information based on a detection result from the specified dose detection pixels 121 (detection units). Additionally, the analog processing unit 402 (the conversion processing unit) of the radiation imaging apparatus 1001 generates and outputs an analog output signal simulating the output of the dose control sensor in the positions corresponding to each receptor field (i.e., the analog output signal for dose control (a signal corresponding to a received dose)).

The digital signal path for dose control (the first signal path) will be described next. This signal transmission path uses a dedicated digital communication path or an equivalent path to transmit a handshake signal for shooting preparations between the high-voltage generation apparatus 1004 and the radiation imaging apparatus 1001.

Handshake operations performed during radiation imaging will be described with reference to FIGS. 4 and 5. With a sequence for determining an irradiation time on the high-voltage generation apparatus 1004, indicated by 5a in FIG. 5, the radiation generation control unit 1042 makes preparations to generate radiation in response to the operator operating the operation switch 46. Once the anode rotation speed of the radiation source 1003 stabilizes and other internal circuits are ready, the signal processing unit 1045 of the high-voltage generation apparatus 1004 outputs a shooting preparation request signal 501 as a request level signal based on a signal input from the radiation generation control unit 1042 (5a in FIG. 5).

The image capturing preparation request signal 501 (request level) output from the signal processing unit 1045 of the high-voltage generation apparatus 1004 is transmitted to the radiation imaging apparatus 1001 through the signal generation unit 1024 of the imaging control apparatus 1002. Then, once the image capturing preparations are complete, the radiation imaging apparatus 1001 outputs a signal indicating that the image capturing preparations are complete. Then, based on a signal input from the radiation imaging apparatus 1001, the signal generation unit 1024 of the imaging control apparatus 1002 outputs an image capturing preparation complete signal 502 as a preparation complete level signal (5a in FIG. 5). The image capturing preparation complete signal 502 (preparation complete level) is input to the radiation generation control unit 1042 through the signal processing unit 1045 of the high-voltage generation apparatus 1004. Here, the signal indicating that image capturing preparations are complete, output from the radiation imaging apparatus 1001, corresponds to the irradiation start signal for starting the irradiation of radiation. The radiation generation control unit 1042 monitors the states of other signals, confirms that the preparations are complete, and then irradiates the radiation 1103. Here, the radiation generation control unit 1042 can control the irradiation of radiation to stop based on a radiation irradiation time set by the operator. The radiation 1103 shifts from an irradiation state to a non-irradiation state under the control of the radiation generation control unit 1042 (irradiation stop control) (5a in FIG. 5).

Then, based on a signal input from the radiation generation control unit 1042, the signal processing unit 1045 of the high-voltage generation apparatus 1004 changes the image capturing preparation request signal 501 to a non-request level and outputs the signal (non-request output). In other words, based on the signal input from the radiation generation control unit 1042, the signal processing unit 1045 outputs the image capturing preparation request signal 501 as a non-request level signal (image capturing preparation request signal 501 (non-request level). The image capturing preparation request signal 501 (non-request level) output from the signal processing unit 1045 of the high-voltage generation apparatus 1004 is transmitted to the radiation imaging apparatus 1001 through the signal generation unit 1024 of the imaging control apparatus 1002. In response to the image capturing preparation request signal 501 (non-request level) signal, the radiation imaging apparatus 1001 shifts the state of the radiation imaging apparatus 1001 from an image capturing preparation complete state to a preparation incomplete state.

An operation sequence performed when a sufficient achieved dose is detected before the set radiation irradiation time passes will be described next with reference to 5b in FIG. 5. The operation sequence is the same as 5a in FIG. 5 until the radiation 1103 is actually irradiated. After that, when a sufficient achieved dose is detected within the radiation imaging apparatus 1001 through a method that will be described later, the signal generation unit 1024 outputs a signal that shifts the image capturing preparation complete signal 502 from the preparation complete level to a preparation incomplete level state (incomplete level), even if the image capturing preparation request signal 501 is at the request level, based on a signal output from the radiation imaging apparatus 1001. Here, when a sufficient achieved dose is detected within the radiation imaging apparatus 1001, the signal output from the radiation imaging apparatus 1001 corresponds to the stop signal (the first stop signal) output from the digital processing unit 401 (the first processing unit) when the dose information obtained based on the first processing (digital signal processing) exceeds the threshold. In the case indicated by 5b in FIG. 5, when a sufficient achieved dose is detected within the radiation imaging apparatus 1001, the state shifts from the preparation complete level to the preparation incomplete level (an incomplete state) after the set radiation irradiation time passes. The image capturing preparation complete signal 502 (incomplete level) is input to the signal processing unit 1045 of the high-voltage generation apparatus 1004 from the signal generation unit 1024. When the image capturing preparation request signal 501 is at the request level and the image capturing preparation complete signal 502 is at the incomplete level, the signal processing unit 1045 outputs, to the signal selection unit 1043, the image capturing preparation complete signal 502 (incomplete state) input from the signal generation unit 1024 as a stop signal for the radiation 1103 on the digital signal path. In other words, the stop signal (the first stop signal) output from the digital processing unit 401 (the first processing unit) is input to the signal selection unit 1043 via the relay unit 1023 of the imaging control apparatus 1002, the signal generation unit 1024, and the signal processing unit 1045 of the high-voltage generation apparatus 1004.

In the case of 5b in FIG. 5, when, for example, the stop signal (the first stop signal) output from the digital processing unit 401 (the first processing unit) is input to the signal selection unit 1043 before the stop signal (the second stop signal) traveling on the analog signal path (the second signal path), the radiation generation control unit 1042 detects that the image capturing preparation complete signal 502 has shifted from the preparation complete state to the preparation incomplete state based on the stop signal (the first stop signal) input to the signal selection unit 1043 first. In other words, the radiation generation control unit 1042 detects that the dose information (the integrated dose) has reached a predetermined dose, and controls the radiation source 1003 to stop irradiating the radiation 1103.

Although the signals are expressed in circuit signal format in FIG. 5, it should be noted that for the image capturing preparation request signal 501 and the image capturing preparation complete signal 502, the communication between the high-voltage generation apparatus 1004 and the radiation imaging apparatus 1001 can also be realized by command communication. In the present embodiment, the signal paths are used for radiation dose control as well as handshake operations during irradiation, and are therefore configured to be capable of transmitting signals for controlling the stopping of radiation irradiation in less than 1 ms, for example. From this perspective, the device used as the signal generation unit 1024 can be a photocoupler, a photo MOS relay, or the like, for example. For command communication, a communication method that can guarantee communication time and delay time can be used, such as, for example, 100BaseTX/1000BaseT by wired communication. Signal paths can also configured using wireless communications by ensuring reliability and responsiveness.

On the other hand, if the specifications specify that the stop function only needs to be triggered during long irradiation periods, such as of about 1 s, for example, when dose suppression is only intended for too much irradiation that does not contribute to an improvement in image quality, the objective can be achieved even with a delay of about 100 ms, for example. The function can therefore be realized using an interface that performs normal shooting handshakes not intended for dose suppression or the like.

Figure 6A:
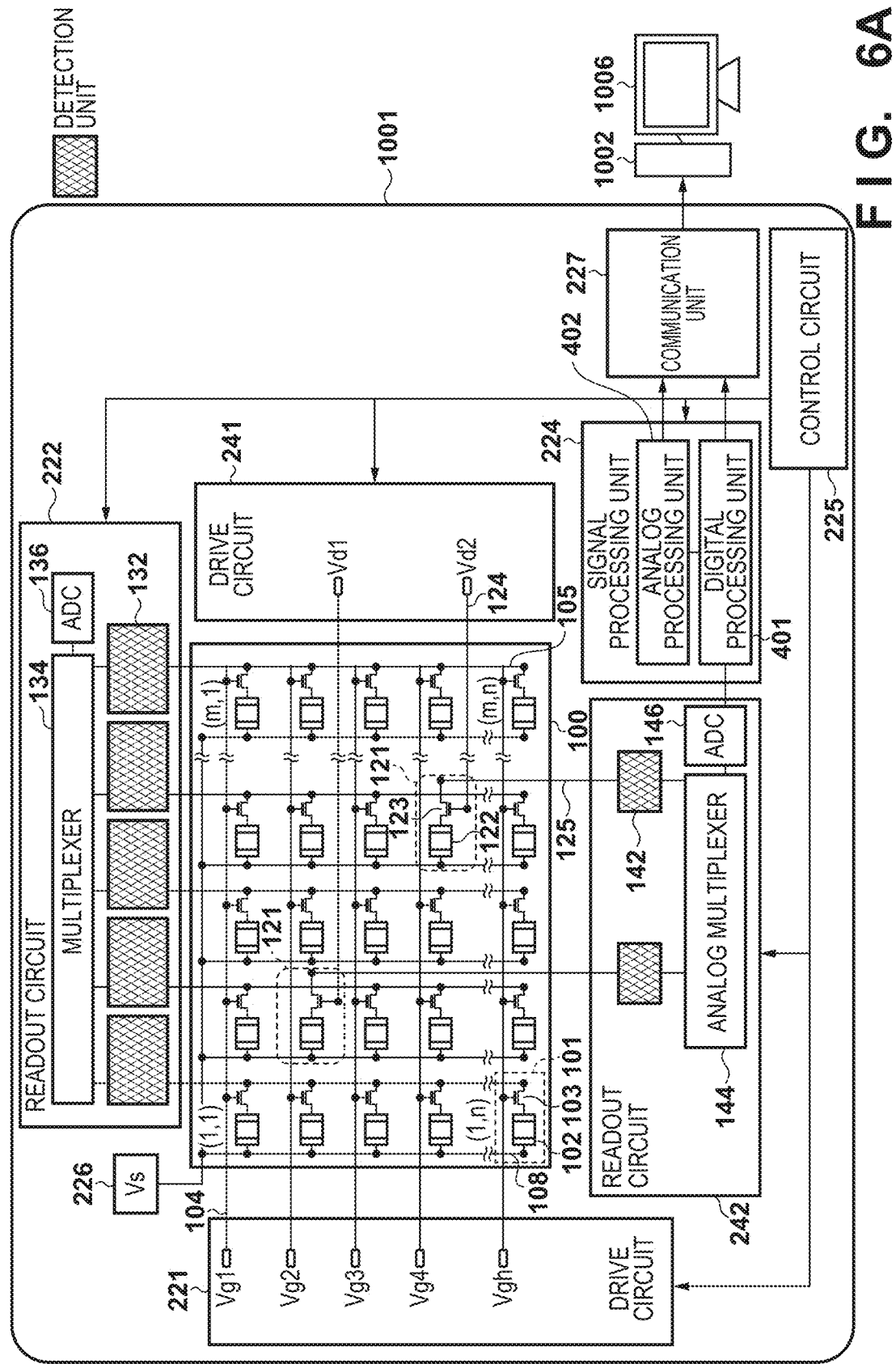
FIG. 6A is a diagram illustrating an example of the internal configuration of the radiation imaging apparatus according to an embodiment.
Figure 6B:
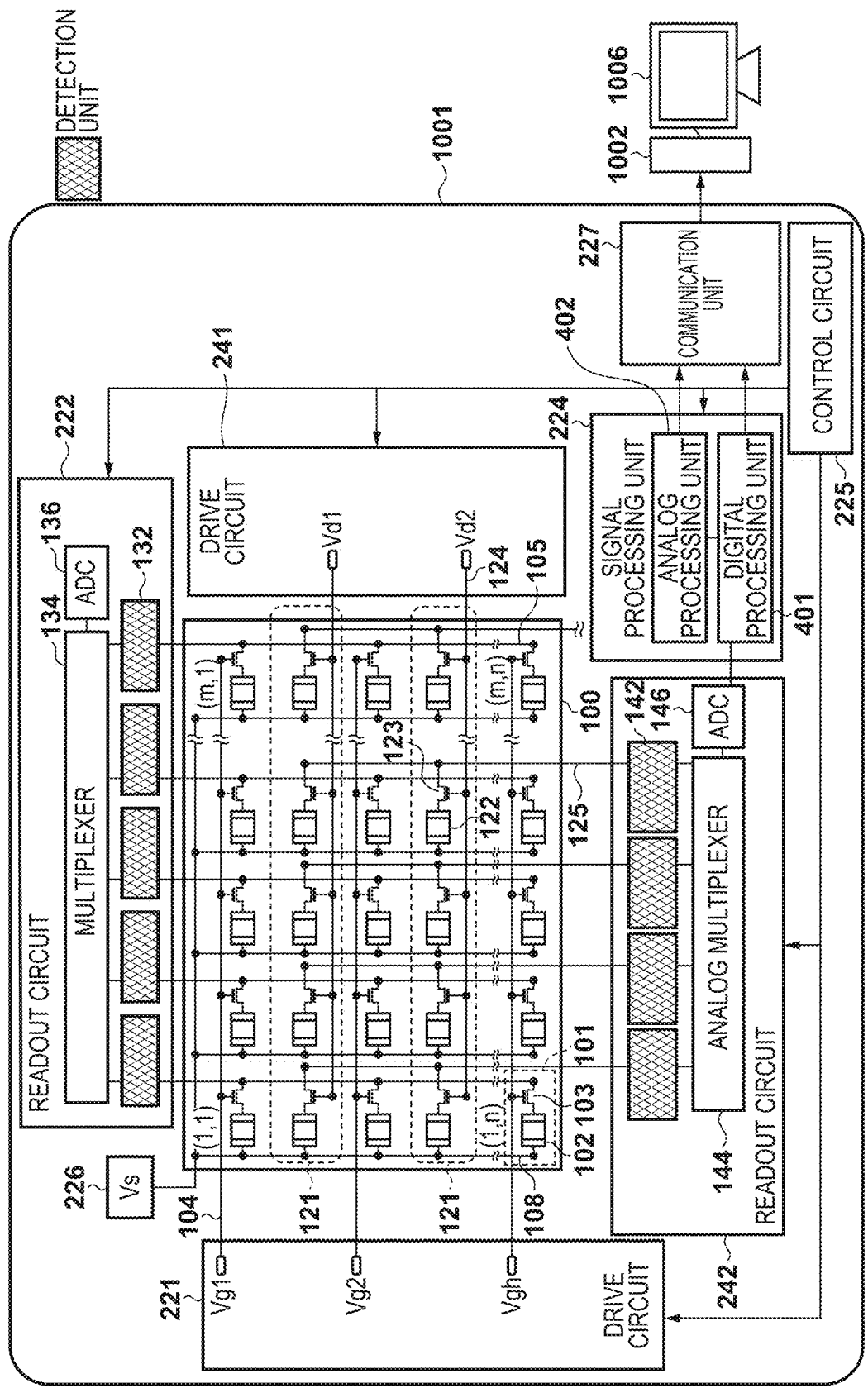
FIG. 6B is a diagram illustrating an example of the internal configuration of the radiation imaging apparatus according to an embodiment.
Figure 6C:
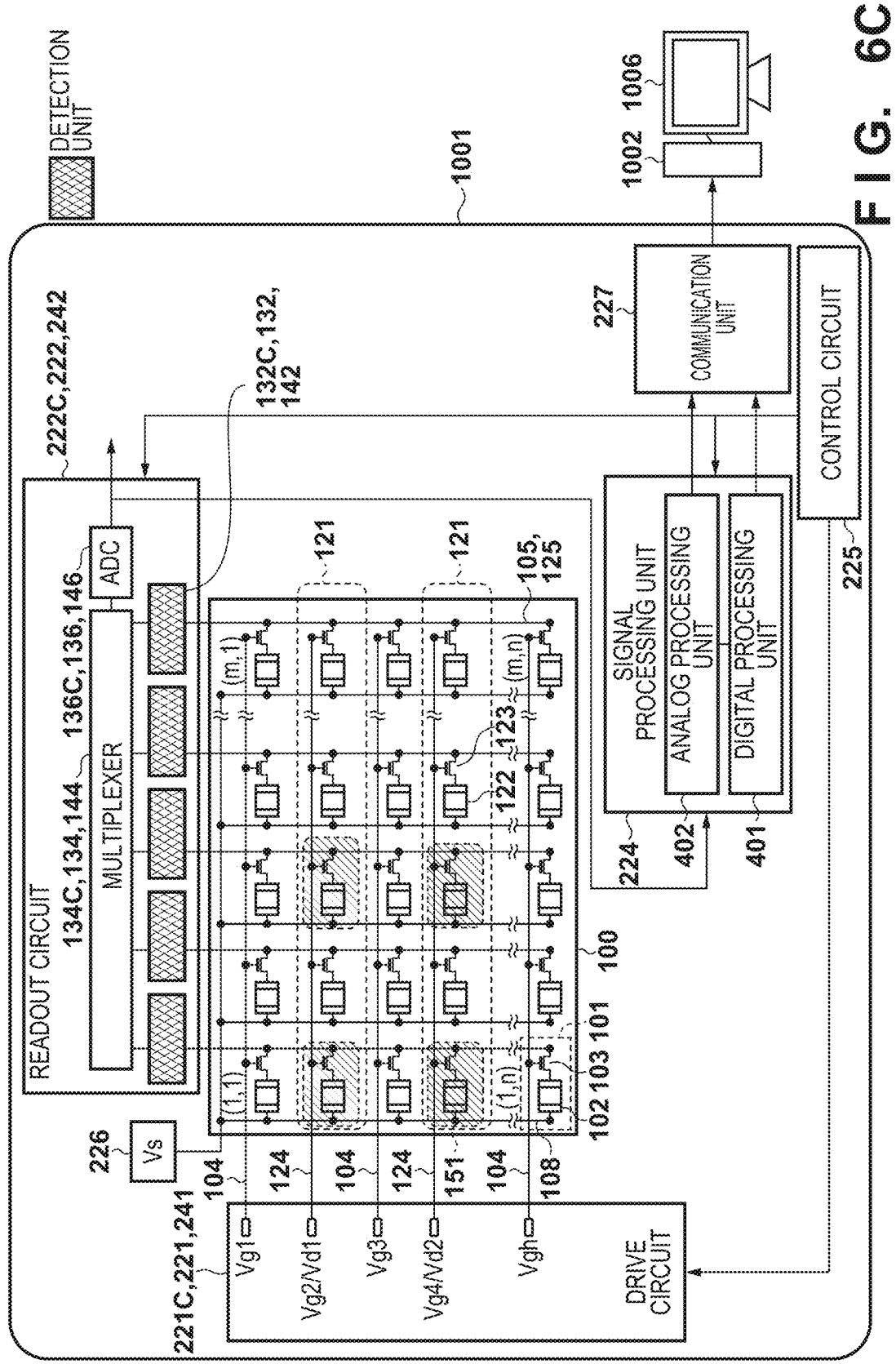
FIG. 6C is a diagram illustrating an example of the internal configuration of the radiation imaging apparatus according to an embodiment.

Operations pertaining to radiation dose detection for the purpose of an automatic exposure function or a dose suppression function will be described next. FIGS. 6A to 6C are diagrams illustrating examples of the internal configuration of the radiation imaging apparatus according to the embodiment.

The radiation imaging apparatus 1001 has a plurality of pixels arranged in the image capturing region 100 to form a plurality of rows and a plurality of columns. The present embodiment will describe an example of a case where each pixel is non-crystalline silicon or polycrystal silicon. The plurality of pixels include a plurality of image capturing pixels 101 for detecting radiation and obtaining a radiation image based on the detected radiation, and the dose detection pixels 121 (detection units) that detect the dose of radiation irradiated from the radiation source.

To accurately control the dose that forms an image through automatic exposure control, it is extremely important that the input/output relationship with respect to radiation be clearly known between the image capturing pixels 101 and the dose detection pixels 121. It is impossible to accurately ascertain the spectrum of the radiation quality of the radiation that has passed through the object and changed for each location in the body. Accordingly, when the outputs of the image capturing pixels 101 for forming an image and the dose detection pixel 121 for automatic exposure control are skewed with respect to the same radiation due to the radiation quality, the skew between the outputs of the image capturing pixels 101 and the dose detection pixels 121 cannot be corrected. Accurate automatic exposure control therefore cannot be performed.

As such, for accurate automatic exposure control, it is necessary to clearly know the input/output relationship with respect to radiation, and the easiest way to achieve this is to make the image capturing pixels 101 and the dose detection pixels 121 exactly the same. In the case of an image sensor that can perform non-destructive readout, such as an image sensor constituted by a CMOS, the image capturing pixels 101 and the dose detection pixels 121 can be made exactly the same. In other words, the functions of image capturing and dose detection can be performed by a single image sensor. In the case of non-crystalline silicon or polycrystal silicon, as in the present embodiment, the destructive readout pixel structure means that non-destructive readout is not possible. The next best option is for the image capturing pixels 101 and the dose detection pixels 121 to be separate pixels, with the structures thereof being similar. This makes it possible to make the output characteristics such as radiation quality dependence identical, with the only difference between the image capturing pixels 101 and the dose detection pixels 121 being minute differences in spatial locations.

The image capturing pixel 101 includes a first conversion element 102 that converts radiation into an electrical signal, and a first switch 103 disposed between a column signal line 105 and the first conversion element 102. The dose detection pixel 121 includes a second conversion element 122 that converts radiation into an electrical signal, and a second switch 123 disposed between a detection signal line 125 and the second conversion element 122.

The first conversion element 102 and the second conversion element 122 are constituted by a scintillator that converts the radiation into light and a photoelectric conversion element that converts the light into an electrical signal. The scintillator is generated formed in a sheet shape to cover the image capturing region 100, and can be shared among a plurality of pixels. Alternatively, the first conversion element 102 and the second conversion element 122 can be constituted by conversion elements which convert radiation directly into light.

The first switch 103 and the second switch 123 can include, for example, a thin-film transistor (TFT) in which an active region is constituted by a semiconductor such as non-crystalline silicon or polycrystal silicon (preferably polycrystal silicon).

The radiation imaging apparatus 1001 has a plurality of column signal lines 105 and a plurality of drive lines 104. Each column signal line 105 corresponds to one of the plurality of columns in the image capturing region 100. Each drive line 104 corresponds to one of the plurality of rows in the image capturing region 100. Each drive line 104 is driven by a drive circuit 221 (a row selection unit).

A first electrode of the first conversion element 102 is connected to a first main electrode of the first switch 103, and a second electrode of the first conversion element 102 is connected to a bias line 108. Here, a single bias line 108 extends in a column direction, and is connected in common to the second electrodes of the plurality of first conversion elements 102 arranged in the column direction. The bias line 108 receives a bias voltage from a power source circuit 226. A second main electrode of each first switch 103 in the plurality of image capturing pixels 101 that constitute a single column is connected to a single column signal line 105. A control electrode of each first switch 103 in the plurality of image capturing pixels 101 that constitute a single row is connected to a single drive line 104.

The plurality of column signal lines 105 are connected to a readout circuit 222. Here, the readout circuit 222 can include a plurality of detection units 132, a multiplexer 134, and an analog-digital converter ("AD converter" hereinafter) 136. Each of the plurality of column signal lines 105 is connected to a corresponding detection unit 132 among the plurality of detection units 132 in the readout circuit 222. Here, a single column signal line 105 corresponds to a single detection unit 132. The detection unit 132 includes, for example, a differential amplifier. The multiplexer 134 selects the plurality of detection units 132 in a predetermined order, and supplies a signal from the selected detection unit 132 to the AD converter 136. The AD converter 136 converts the supplied signal into a digital signal and outputs the digital signal.

A first electrode of the second conversion element 122 is connected to a first main electrode of the second switch 123, and a second electrode of the second conversion element 122 is connected to the bias line 108. A second main electrode of the second switch 123 is electrically connected to the detection signal line 125. A control electrode of the second switch 123 is electrically connected to a drive line 124. The radiation imaging apparatus 1001 can include a plurality of detection signal lines 125. One or more dose detection pixels 121 can be connected to a single detection signal line 125. The drive line 124 is driven by a drive circuit 241. One or more dose detection pixels 121 can be connected to a single drive line 124.

The detection signal line 125 is connected to a readout circuit 242 (AEC sensor readout circuit). Here, the readout circuit 242 can include a plurality of detection units 142, a multiplexer 144, and an AD converter 146. Each of the plurality of detection signal lines 125 is connected to a corresponding detection unit 142 among the plurality of detection units 142 in the readout circuit 242. Here, a single detection signal line 125 corresponds to a single detection unit 142. The detection unit 142 includes, for example, a differential amplifier. The multiplexer 144 selects the plurality of detection units 142 in a predetermined order, and supplies a signal from the selected detection unit 142 to the AD converter 146. The AD converter 146 converts the supplied signal into a digital signal and outputs the digital signal.

The output of the AD converter 146 of the readout circuit 242 is supplied to a signal processing unit 224, and is processed by the signal processing unit 224. Based on the output of the AD converter 146 of the readout circuit 242, the signal processing unit 224 outputs information indicating irradiation of radiation to the radiation imaging apparatus 1001.

The signal processing unit 224 of the radiation imaging apparatus 1001 of the present embodiment includes: the digital processing unit 401, which outputs the stop signal when the dose information, obtained based on the first processing (digital signal processing) performed on the result of the detection by the dose detection pixels 121 (detection units), exceeds a threshold; and the analog processing unit 402 (conversion processing unit), which outputs a signal obtained by performing the second processing (analog conversion processing) on the signal subjected to the first processing (digital signal processing) by the digital processing unit 401.

Specifically, for example, the digital processing unit 401 detects the irradiation of radiation on the radiation imaging apparatus 1001, computes a radiation irradiation amount and/or an integrated irradiation amount, and the like. For use in such applications, the earlier second conversion element 122 is configured having a pixel count ratio that is no greater than 1% of the first conversion elements 102, which correspond to the original image sensor. This is to suppress the amount of radiation that does not contribute to image formation to less than the amount absorbed by existing AEC sensors. In order to handle a variety of measurements, it is useful to have the second conversion elements 122 distributed uniformly or in a central part where the region of interest is centered, to increase the density in a peripheral part for use in irradiation area detection, or the like.

The analog processing unit 402 converts the irradiation dose, which has been subjected to digital signal processing by the digital processing unit 401, into analog, and generates an analog output signal simulating the output of the dose control sensor (an ion chamber/phototimer or the like). The control circuit 225 controls the drive circuits 221 and 241 and the readout circuits 222 and 242 based on information from the signal processing unit 224. Based on information from the signal processing unit 224, the control circuit 225 generates signals that can express, for example, the start and end of exposure (the accumulation of charges corresponding to the irradiated radiation by the image capturing pixels 101). The radiation imaging apparatus 1001 also includes the communication unit 227, which handles communication with the imaging control apparatus 1002. The communication unit 227 includes two communication units, namely a wired communication unit and a wireless communication unit, for outputting signals over the signal path for digital signals (the first signal path), and an analog output unit that outputs an analog output signal (the analog output signal for dose control) simulating the output of a dose control sensor over the signal path for analog signals (the second signal path). In other words, the communication unit 227 outputs, over the digital signal path (the first signal path) the signal output from the digital processing unit 401 (the first processing unit), and outputs, over the analog signal path (the second signal path), the signal output from the analog processing unit 402 (the conversion processing unit).

FIG. 6A illustrates an example in which the dose detection pixels 121 are disposed in 1×1 pixel units, whereas FIGS. 6B and 6C illustrate examples in which the dose detection pixels 121 are arranged in units of single rows, such as m×1. When the dose detection pixels 121 are disposed in units of single rows, such as m×1, line profiles can be generated in real time, and the detection information of the dose detection pixels 121 can be used for real-time irradiation dose determination through more advanced image processing, as well as for processing for the purpose of such determination.

Additionally, FIGS. 6A and 6B illustrate examples in which the image capturing pixels 101 and the dose detection pixels 121 are read out by separate and independent circuit configurations (the readout circuit 222 and the readout circuit 242), whereas FIG. 6C illustrates a configuration in which the image capturing pixels 101 and the dose detection pixels 121 are read out by a shared circuit configuration.

In FIG. 6C, the readout circuit used as both the readout circuit 222 and the readout circuit 242 is indicated by "222C", and the drive circuit used as both the drive circuit 221 and the drive circuit 241 is indicated by "221C".

Additionally, in FIG. 6C, the detection unit used as both the detection unit 132 and the detection unit 142 is indicated by "132C", the multiplexer used as both the multiplexer 134 and the multiplexer 144 is indicated by "134C", and the AD converter used as both the AD converter 136 and the AD converter 146 is indicated by "136C".

With the circuit configuration in FIG. 6C, the control of the shared drive circuit 221C and readout circuit 222C is slightly more complicated, but the drive circuit 241, the readout circuit 242, and the like of each dose detection pixel 121 is shared with the drive circuit 221 and the readout circuit 222 of each image capturing pixel 101, which is advantageous in terms of quality and costs, in that the circuit configuration is simplified and the number of components is reduced.

Furthermore, with the circuit configuration illustrated in FIG. 6C, the dose detection pixels 121 can be used as image capturing pixels 101 in cases of shooting that does not use the dose detection pixels 121. Additionally, correction pixels 151 are provided, as indicated by the hatching in FIG. 6C. The correction pixels 151 are constituted by at least one pixel used to correct the irradiation amount of the radiation, and the sensitivity of the correction pixels 151 to radiation is set to be lower than the sensitivity of the image capturing pixels 101 to radiation. Although the correction pixels 151 have basically the same structure as the dose detection pixels 121 and the image capturing pixels 101, the structure differs from that of the dose detection pixels 121 and the image capturing pixels 101 in that the second conversion elements 122 are covered by a film that shields visible light from the exterior. The shielding of light from the correction pixels 151 is achieved by covering the second conversion elements 122 with a metal layer such as aluminum, for example.

The radiation imaging system 1000 of the present embodiment includes the radiation imaging apparatus 1001, which includes the dose detection pixels 121 that detect the dose of radiation irradiated from the radiation source 1003, and the imaging control apparatus 1002 that controls the radiation imaging apparatus 1001. Here, the imaging control apparatus 1002 specifies the position of the dose detection pixel in the region of interest (the receptor field 1012) for calculating the dose indicator value of the radiation image before radiation imaging, determines a threshold in accordance with the position of the dose detection pixel, and transmits the position of the dose detection pixel and the threshold to the radiation imaging apparatus 1001. The control circuit 225 of the radiation imaging apparatus 1001 sets the position of the dose detection pixel and the threshold in the region of interest (the receptor field 1012) transmitted from the imaging control apparatus 1002, and captures an image based on that setting.

An example of the operations of the dose detection pixels 121 in FIG. 6C will be described here with reference to the timing chart in FIG. 7. These operations are executed by the control circuit 225, which controls the drive circuit 221C and the readout circuit 222C, and the signal processing unit 224 operating in tandem. Accordingly, the combination of the signal processing unit 224 and the control circuit 225 may be called an exposure determination unit.

Figure 7:
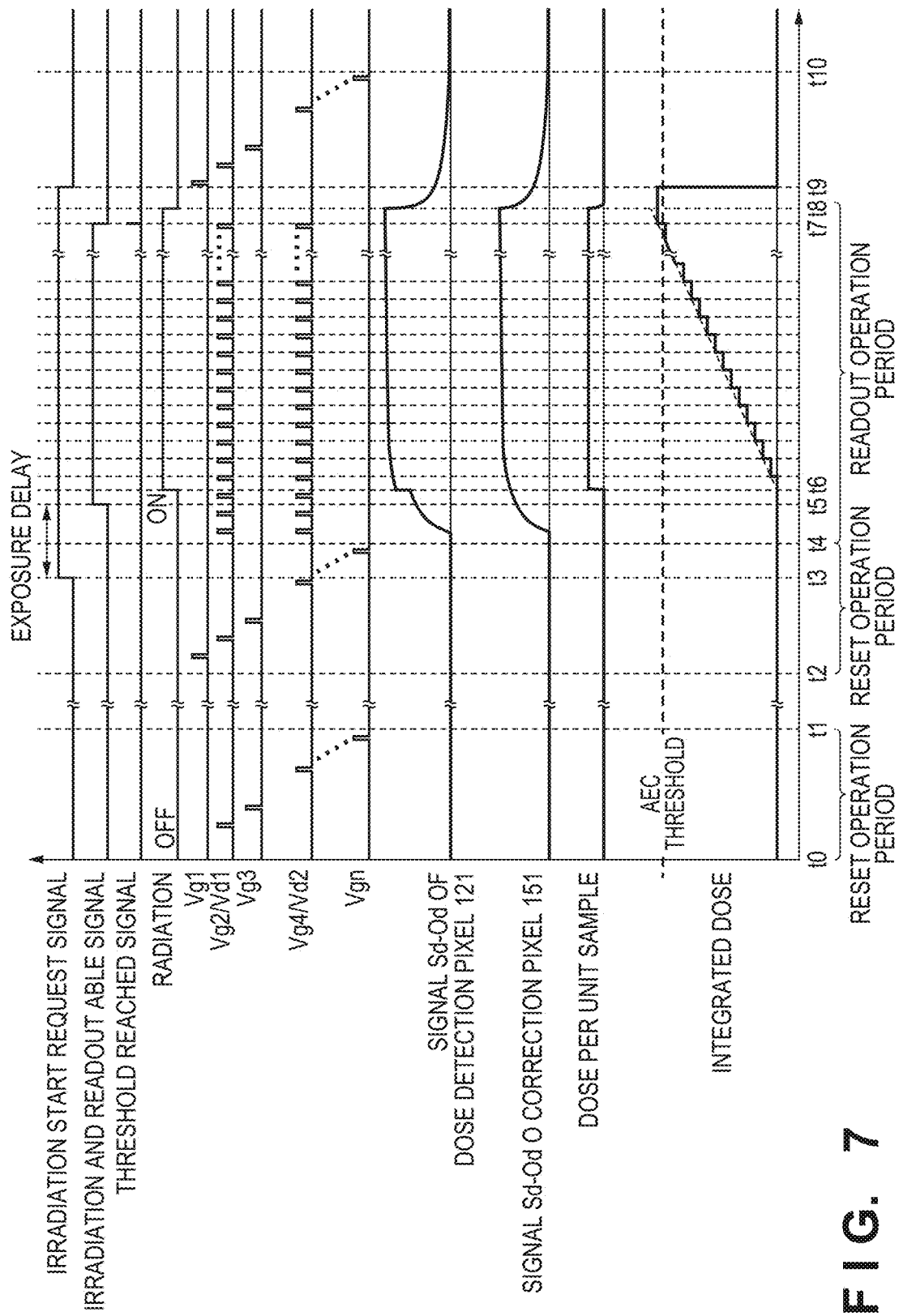
FIG. 7 is a timing chart illustrating internal operations of the radiation imaging apparatus of an embodiment.

In FIG. 7, "radiation" indicates whether or not the radiation imaging apparatus 1001 is irradiated with radiation. In the case of low (the signal is OFF), no radiation is irradiated, whereas in the case of high (the signal is ON), radiation is irradiated.

"Vg1" to "Vgn" indicate drive signals supplied from the drive circuit 221C to the plurality of drive lines 104. "Vgk" indicates the drive signal supplied to the drive line 104 in the kth row (where k=1, . . . , number of drive lines n). Some of the plurality of drive lines supplied by the drive circuit 221C function as the drive lines 124 that supply drive signals for driving the dose detection pixels 121 or the correction pixels 151. "Vgk/Vdj" corresponds to the drive line in the kth row and the drive line 124 in a jth detection drive line (where k=1, . . . , number of drive lines n, and j=1, . . . , number of detection drive lines). For example, "Vg2/Vd1" indicates the drive signal supplied to the drive line 124, which indicates the drive line in the second row and the first detection drive line.

"Dose detection pixel signal" indicates the value of the signal read out from the dose detection pixel 121. "Correction pixel signal" indicates the value of the signal read out from the correction pixel 151. "Integrated irradiation amount" indicates the integrated value of the radiation irradiated on the radiation imaging apparatus 1001. A method for determining this integrated value will be described later.

A period from time t0 to t4 is a "reset operation period". At time t0, the control circuit 225 starts reset operations of the plurality of pixels. The reset operations are operations for removing the charge accumulated in the conversion element of each pixel, and specifically are operations for putting the switch elements (the first switch 103 and the second switch 123) of each pixel into a conductive state by supplying drive signals from the drive circuit 221C to the drive lines 104 and 124. The control circuit 225 resets each pixel connected to the drive line 104 in the first row by controlling the drive circuit 221C. The control circuit 225 then resets each pixel connected to the drive line 124 in the second row. The control circuit 225 repeats these operations until the drive line 104 in the last row. At time t1, the control circuit 225 finishes the reset operations of the drive line 104 in the last row, and then repeats the reset operations starting from the drive line 104 in the first row again.

At time t3, an "irradiation start request signal" is activated by the transmission of the irradiation start request signal from the imaging control apparatus 1002 to the control circuit 225. At this point in time, shooting condition settings are finalized by the information transmitted from the imaging control apparatus 1002. A maximum irradiation time of radiation and, in some cases, irradiation area information, direct radiation dose information, automatic exposure control signals, and information during automatic exposure (ROI/calculation method) are transmitted from the imaging control apparatus 1002 to the control circuit 225 of the radiation imaging apparatus 1001. The control circuit 225 can use the information transmitted from the imaging control apparatus 1002 as correction information for AEC operations.

Upon receiving the irradiation start request signal, the control circuit 225 performs the reset operations until the last row and then completes the reset operations. The control circuit 225 may end the reset operations before performing the reset operation to the last row, and move to the next process. For example, upon receiving the irradiation start request signal during the reset operations of the drive line 104 (124) in the kth row, the control circuit 225 can perform control to move to the next process without performing the reset operations of the drive lines 104 (124) in the k+1th and subsequent rows. In this case, step-shaped image artifacts may occur in the vicinity of the k+1th row, but it is possible to reduce the step-shaped image artifacts by adjusting the drive performed when obtaining a correction image for correcting the radiation image, such as by terminating the driving at the k+1th row in a similar manner, as well as by performing image processing on the radiation image.

A period from time t4 to t8 is a "readout operation period". At time t4, the control circuit 225 starts measurement operations for measuring the amount of radiation being irradiated on the radiation imaging apparatus 1001. In the measurement operations, the control circuit 225 repeatedly executes readout operations that read out from the dose detection pixels 121 and the correction pixels 151. Of the readout operations performed a plurality of times, at least one of the readout operations in the first half are performed to determine a correction value, and the readout operations repeated in the second half are performed to continuously measure the amount of radiation at each time.

At time t5, the control circuit 225 activates an "irradiation and readout able signal". The readout operations during the active period of the "irradiation and readout able signal" are performed only for drive line 124 (an AEC drive line) and not for the other drive lines 104. Specifically, the control circuit 225 supplies drive signals to the drive lines 124 (AEC drive lines), among the plurality of drive lines 104 and 124, that are connected to at least one of the dose detection pixel 121 and correction pixel 151. The control circuit 225 does not supply drive signals to the drive lines 104, among the plurality of drive lines 104 and 124, that are not connected to any of the dose detection pixels 121 and correction pixels 151.

Additionally, the control circuit 225 may perform driving to simultaneously supply drive signals to the drive lines 124, among the plurality of drive lines 104 and 124, that are connected to at least one of the dose detection pixel 121 and correction pixel 151. As a result, signals from a plurality of pixels connected to the same drive line are simultaneously read out by the readout circuit 222C. Because the image capturing pixels 101 (including the dose detection pixels 121 and the correction pixels 151) are connected to column signal lines 105C (105 and 125) but are read out selectively by the control circuit 225, the readout circuit 222C can read out signals for AEC detection separately from signals for image detection.

The control circuit 225 performs the readout operations a predetermined number of times, i.e., at least once, to determine the correction value. The signal processing unit 224 determines a correction value Od based on the signal read out from the dose detection pixel 121 by a predetermined number of readout operations, and a correction value Oc based on the signal read out from the correction pixel 151 by this predetermined number of readout operations.

The determination of the correction values Od and Oc will be described next. The parameters for determining the correction values are actually constituted by outputs from a plurality of pixels, and which pixels are used, how the pixels are used, and the like will be described later.

If the predetermined number of times of the readout operations is one, there is only one signal per pixel read out from the dose detection pixels 121, and thus the signal processing unit 224 takes the value of that signal as the correction value Od. If the predetermined number of times is multiple times, the signal processing unit 224 takes the average value of the plurality of signals read out as the correction value Od. Other statistical values can be used instead of the average value, and the value of the correction value (an offset signal) is denoted as Od. Based on the signal read out from the correction pixel 151, the correction value Oc can also be determined in a similar manner, i.e., Oc as the value of the correction value (an offset signal). The signal processing unit 224 stores the correction values Od and Oc determined in this manner in a storage unit 172, and can use the values in subsequent processing.

Because the value of the offset signal changes depending on the temperature environment of the sensor and the like, obtaining the offset signal immediately before radiation detection, as in the present embodiment, makes it possible to reduce the difference between the offset signal obtainment and an offset component at the time of radiation detection, and the offset component at the time of radiation detection can be accurately corrected.

Conversely, there may be a case where error due to a random noise component is higher than a fluctuation component due to temperature changes or the like during the "readout operation period" (time t4 to t8) because the number of samples for generating the correction values Od and Oc is small. In such a case, for example, it is possible to generate the correction values Od and Oc at a timing where there is a surplus of time, such as during the reset operation period, when a sufficient number of sampling times can be secured and error due to random noise components such as thermal noise can be suppressed.

The time from when the "irradiation start request signal" is transmitted from the imaging control apparatus 1002 to the control circuit 225 until the control circuit 225 transmits the "irradiation and readout able signal" to the high-voltage generation apparatus 1004 via the imaging control apparatus 1002 is called "exposure delay". In this case, it is no longer necessary to obtain data during the period from t4 to t5 (the "exposure delay" period), and the period corresponding to the exposure delay can be shortened.

After completing the readout operations of the correction values Od and Oc at least one time, the control circuit 225 transmits the "irradiation and readout able signal" to the high-voltage generation apparatus 1004 via the imaging control apparatus 1002 at time t5. The control circuit 225 repeatedly executes the readout operations described above after the active transmission of the irradiation and readout able signal. The signal processing unit 224 measures an "integrated DOSE" as the integrated value of the dose of radiation (described later) for each readout operation, and determines whether the integrated value exceeds a pre-set "AEC threshold". At time t5, the control circuit 225 sends the "irradiation and readout able signal" to the high-voltage generation apparatus 1004, after which the irradiation of radiation begins at time t6.

A method for determining the radiation dose DOSE is described below. The value of the signal read out from the dose detection pixel 121 by the most recent readout operation is indicated by Sd. The value of the signal read out from the correction pixel 151 by the most recent readout operation is indicated by Sc. The signal processing unit 224 calculates the radiation dose DOSE by applying Sd, Sc, Od and Oc to the Formulas (1) and (2) below. Because the "AEC threshold" corresponds to the dose per unit of area, Formula (2), which indicates an integrated radiation dose DOSE, is similarly normalized to the dose per unit of area for comparison. Based on the signal read out from the correction pixel 151 from which visible light is shielded, the control circuit 225 of the radiation imaging apparatus 1001 a signal read out from the dose detection pixel 121 in the region of interest (the receptor field 1012) specified by the imaging control apparatus 1002, and calculates the integrated dose of the radiation based on the signal corrected.

$$\text{DOSE per unit sample} = (Sd - Od) - (Sc - Oc) \quad (1)$$

$$\text{Integrated DOSE} = \Sigma\{(Sd - Od) - (Sc - Oc)\} \quad (2)$$

The DOSE per unit sample indicated in FIG. 7 is an example of the calculation result of Formula (1) above. In actuality, this is a discrete value that is updated each time the irradiated radiation is read out by supplying a drive signal to each of the drive lines 124 (AEC drive lines) and causing the dose detection pixels 121 to operate, but is illustrated as being continuous in FIG. 7. The integrated DOSE indicated in FIG. 7 is an example of the calculation result for the integrated DOSE of Formula (2) above. FIG. 7 illustrates a trend in which the integrated DOSE is updated and increases with each readout.

The signal processing unit 224 obtains a difference (Sd−Od) between (i) the value Sd of the signal read out from the dose detection pixel 121 after the control circuit 225 has transmitted the irradiation and readout able signal and (ii) the correction value Od determines based on the signal read out from the dose detection pixel 121 before transmitting the irradiation and readout able signal. The signal processing unit 224 also obtains a difference (Sc−Oc) between (i) the value Sc of the signal read out from the correction pixel 151 and (ii) the correction value Oc determined based on the signal read out from the correction pixel 151 before transmitting the irradiation and readout able signal. Then, the signal processing unit 224 calculates the radiation dose DOSE (DOSE per unit sample) and the integrated DOSE based on the obtained difference (Sd−Od) and difference (Sc−Oc).

As illustrated in FIG. 7, the "dose detection pixel 121 signal (Sd−Od)", which is the signal read out from the dose detection pixel 121 that is not shielded, changes significantly immediately after the end of the reset operations (immediately after time t4) and stabilizes over time, for example, at approximately 100 ms. As such, even if the radiation dose DOSE is calculated using only the value Sd and the correction value Od of the signal obtained from the dose detection pixel 121, the offset amount will not be sufficiently removed. If the start of the readout operation for obtaining the correction value Od is delayed until the signal read out from the dose detection pixel 121 stabilizes, the time from when the irradiation start request signal is transmitted to when radiation exposure actually starts (the time from time t3 to t5, i.e., the exposure delay) lengthens.

In the circuit configuration illustrated in FIG. 6C, the value Sc of the signal read out from the correction pixel 151 and the correction value Oc are further used to measure the radiation dose DOSE. Because the sensitivity of the correction pixel 151 to radiation is lower than the sensitivities of the dose detection pixel 121 and the image capturing pixel 101 to radiation, the value Sc of the signal read out from correction pixel 151 after the start of the irradiation of radiation can be regarded as representing the offset component of the value Sd of the signal read out from dose detection pixel 121. Furthermore, in the present embodiment, the radiation dose DOSE is determined using the correction values Od and Oc based on the signals read out from the dose detection pixel 121 and the correction pixel 151 before the start of the irradiation of radiation. This makes it possible to correct inherent characteristic differences in each pixel (e.g., differences in detection circuit channels, differences in the parasitic resistance and parasitic capacitance in each pixel and the like).

At time t7 in FIG. 7, the integrated DOSE has reached the AEC threshold pre-set by the control circuit 225. In response, the control circuit 225 transmits information indicating that the AEC threshold has been reached, by transmitting the "threshold reached signal" to the high-voltage generation apparatus 1004 via the imaging control apparatus 1002, by deactivating the "irradiation and readout able signal", or the like. The imaging control apparatus 1002 controls irradiation from the radiation source such that the dose target value set as the threshold and the dose indicator value in the radiation image become equal. Instead of transmitting the threshold reached signal to the imaging control apparatus 1002 at the timing when the integrated DOSE reaches the AEC threshold, the control circuit 225 may estimate the time when the integrated irradiation amount will reach the threshold and transmit the threshold reached signal at the estimated time. Having received the threshold reached signal via the imaging control apparatus 1002 to report that the AEC threshold has been reached, the high-voltage generation apparatus 1004 ends the irradiation of radiation at time t8.

Note that in order to accurately integrate the irradiation dose and stop the irradiation of radiation at an appropriate response time, the readout cycle of the drive lines 124 (the AEC drive lines) Vgk/Vdj may be a sufficiently short cycle compared to the actual irradiation time, e.g., no greater than 1/10 at the longest. Normally, when an amorphous silicon sensor is used, it takes 10 µs to 50 µs to read out a single row of signals. Therefore, in order to read out a broad area, it is necessary to make settings such that the overall operations of the dose detection pixels 121 fit into an optimal time, by simultaneously enabling a plurality of drive lines 124 (AEC drive lines) Vgk/Vdj and reading out the outputs thereof or the like. Similarly, particularly in cases where the actual irradiation time is no greater than a few ms, the delay time from when the integrated radiation irradiation is detected to when the "threshold reached signal" is output after the comparison of the reached threshold to the AEC threshold can be set to 1 ms or less, for example. It is also possible to perform control by setting the AEC threshold smaller by the delay time, taking into account the delay time in advance according to the slope of the integrated dose.

At this time, the control circuit 225 also transmits, to the imaging control apparatus 1002, the "information during automatic exposure (ROI/calculation method)", the achieved dose information, and the like that are actually employed.

From time t7 to time t9 to t10, which is a predetermined time after the passage of at least an assumed delay time until the radiation stops, the drive circuit 221C again supplies the drive signals Vg1 to Vgn to the plurality of drive lines 104, the readout circuit 222C reads out signals from the plurality of image capturing pixels 101, and the signals processed by the readout circuit 222C are transmitted from the communication unit 227 to the imaging control apparatus 1002 through the signal processing unit 224. The imaging control apparatus generates a radiation image based on the signals transmitted from the communication unit 227 of the radiation imaging apparatus 1001, and performs image processing on the generated radiation image. The radiation image generated and processed by the imaging control apparatus 1002 is transmitted to the display unit 1006 through the imaging control apparatus 1002.

In the above-described example, the control circuit 225 starts a predetermined number of readout operations to determine the correction values Od and Oc immediately after the reset operations. Instead, the control circuit 225 may start a predetermined number of readout operations after a predetermined time (e.g., several ms to several tens of ms) has passed following the completion of the reset operations. This makes it possible to suppress signal readout during periods of particularly large time fluctuations.

With respect to the calculation of the general dose indicator value EI, there are two typical examples, namely a case where the calculation region of the dose indicator value EI is not changes according to differences in image based on the protocol, the shooting attitude of the object, the image capturing site, or the like, and a case where the calculation region of the dose indicator value EI is changed. When the calculation region of the dose indicator value EI is not changed, the method calculates the dose indicator value EI in a fixed ROI, and the dose indicator value EI is calculated in a pre-determined region (the fixed ROI) of the image capturing apparatus. This provides an advantage in that the operator can clearly distinguish the area of the image in which the calculation is performed. On the other hand, a fixed ROI has a disadvantage in that it is difficult to set the dose target value EIt, manage the deviation DI, and the like because of the large variation in the differences among protocols caused by differences in the object.

In contrast, when changing the calculation region of the dose indicator value EI, the control circuit 225 first specifies an EI value calculation region for calculating the dose indicator value EI for each instance of shooting, sets the specified EI value calculation region as the ROI for calculating the EI value, and calculates the dose indicator value EI by obtaining a representative value in the set ROI.

Although it is difficult for the operator to know in which area the dose indicator value EI is calculated during shooting, the set ROI can be confirmed by sharing the calculation algorithm with the operator in advance, by displaying the ROI used after the calculation as necessary, and the like. Furthermore, because the dose indicator value EI is calculated after the irradiation area is specified, the variation due to differences in protocols, object images, and the like is smaller than with a fixed ROI, and a medical facility can accurately control the dose during shooting by setting the dose target value EIt and managing the deviation DI.

From the perspective of appropriately managing the irradiation dose, which is the purpose of introducing the dose indicator value EI, it is better to be able to calculate the dose indicator value EI by changing the area (setting the ROI) while being aware of the effective area of the actual image than to calculate the dose indicator value EI in a fixed ROI where the region of the image capturing apparatus does not change regardless of the conditions of the object (e.g., the shooting attitude of the object, the image capturing site, and the like).

Figure 8:
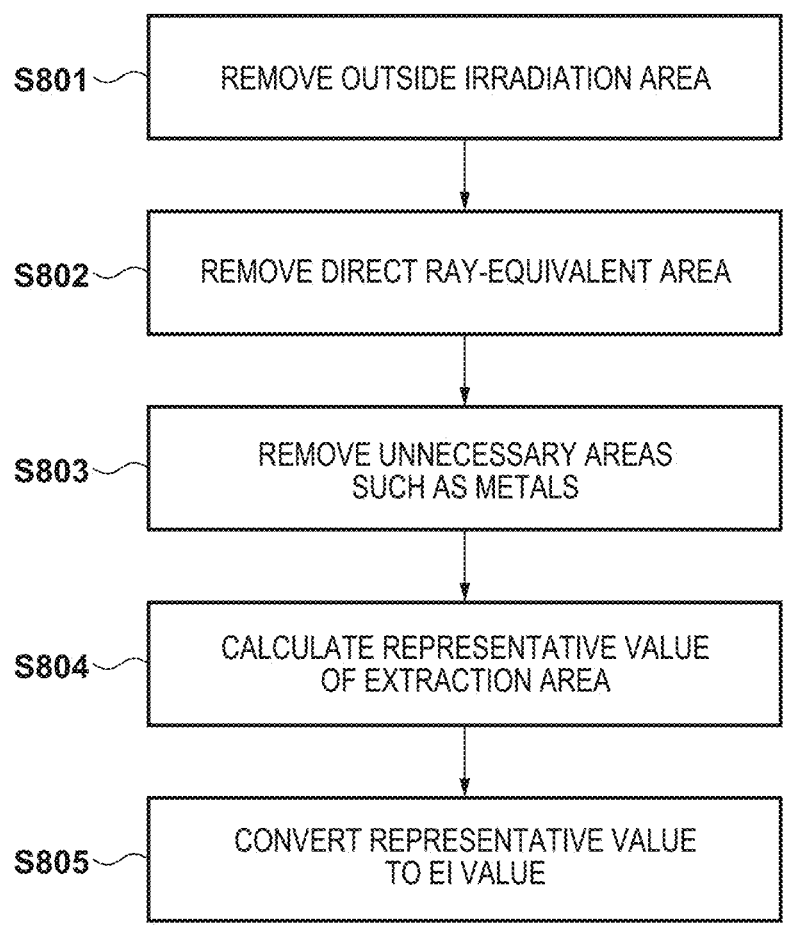
FIG. 8 is a diagram illustrating the flow of processing for calculating a dose indicator value.

FIG. 8 is a flowchart illustrating the flow of processing for calculating the dose indicator value EI. FIG. 8 illustrates a sequence for calculating the dose indicator value EI from an image after shooting. First, in step S801 (removing the outside of the irradiation area), regions that are not irradiated with irradiation area and are clearly outside the region of interest in the diagnostic image are excluded from the area for calculating the dose indicator value EI of the captured image. A method of calculation based on collimator information and tube-FPD distance (FDD) information, extraction of irradiation and regions from the image using prior captured site information, AI-based determination using machine learning, and the like can be used as the processing method.

Next, in step S802 (direct ray equivalent region removal), direct ray regions including grid-only regions are specified and regions outside the region of interest are excluded from the area for calculating the dose indicator value EI. An empirical fixed-threshold method, a modal method, a differential histogram method, a p-tile method, a discriminant analysis method, or the like can be used as the processing method.

Furthermore, in step S803 (removal of unnecessary areas such as metals), low-dose regions that are within the region of interest but should not be used as dose indicators for the region of interest in a normal diagnostic image are excluded from the area for calculating the dose indicator value EI. The area growth method, the snake method, or the like can be used as the processing method. The processing up to this point (S801 to S803) can determine the area for calculating the dose indicator value EI in the captured image as an extraction area.

Next, in step S804 (calculation of the representative value of the extraction area), a representative value such as the average value or the median value of the pixel values in the area for calculating the dose indicator value EI (the extraction area; the region of interest) is calculated. Finally, in step S805 (converting the representative value to the EI value), the representative value calculated in step S804 is converted such that, for example, 100=1 µGy, and the dose indicator value EI is calculated. The deviation DI between the calculated dose indicator value EI and the dose target value EIt is also calculated. Based on the calculated deviation DI, the operator can confirm whether the radiation image was shot with the expected radiation dose. Currently, even if the deviation DI can be confirmed, which modifications should be performed to reduce the deviation DI often has to be obtained through trial and error by hospital facilities, including by operators.

Figure 9:
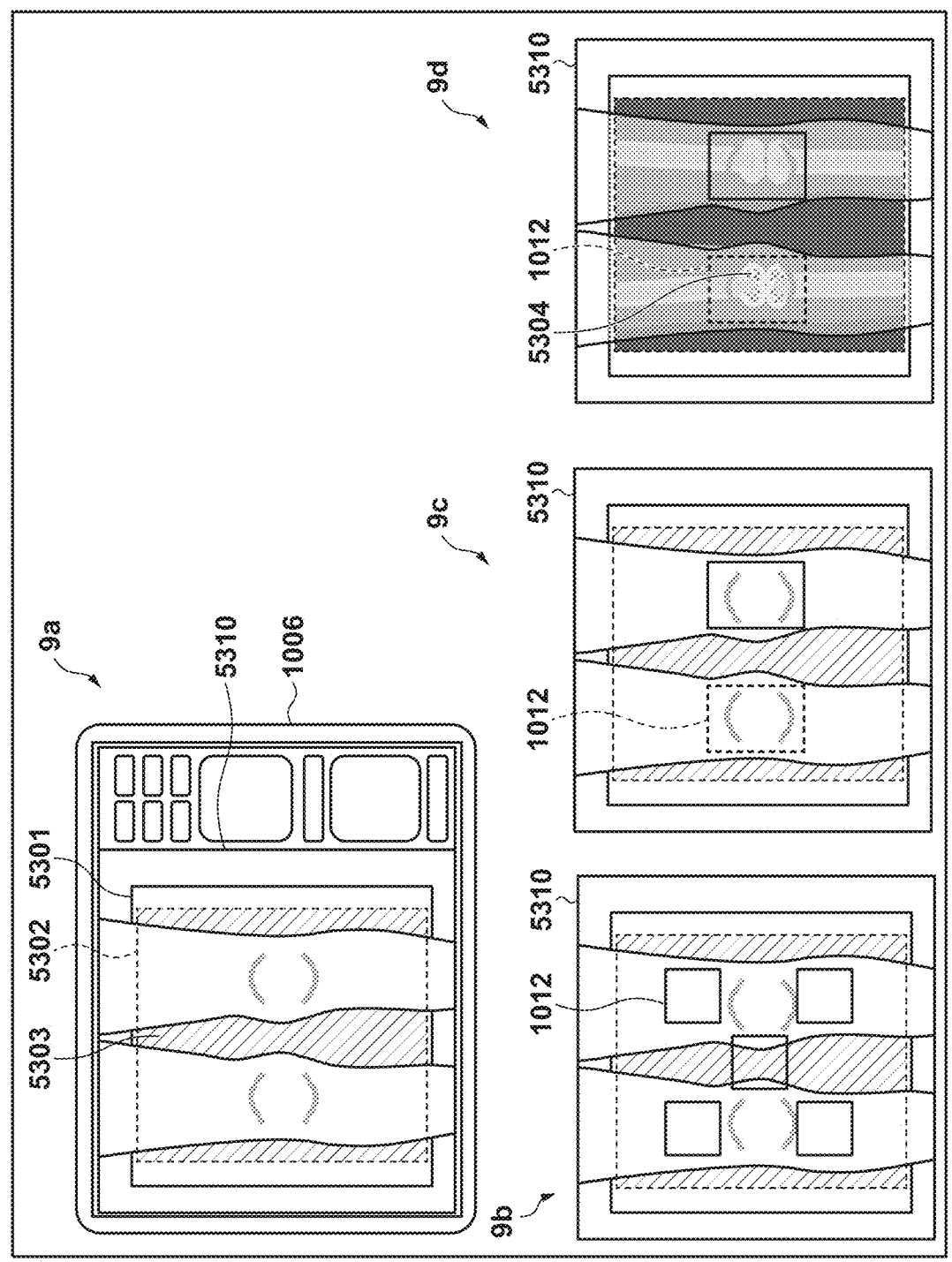
FIG. 9 is a diagram illustrating pre-irradiation adjustment in a method for calculating the dose indicator value.
Figure 10:
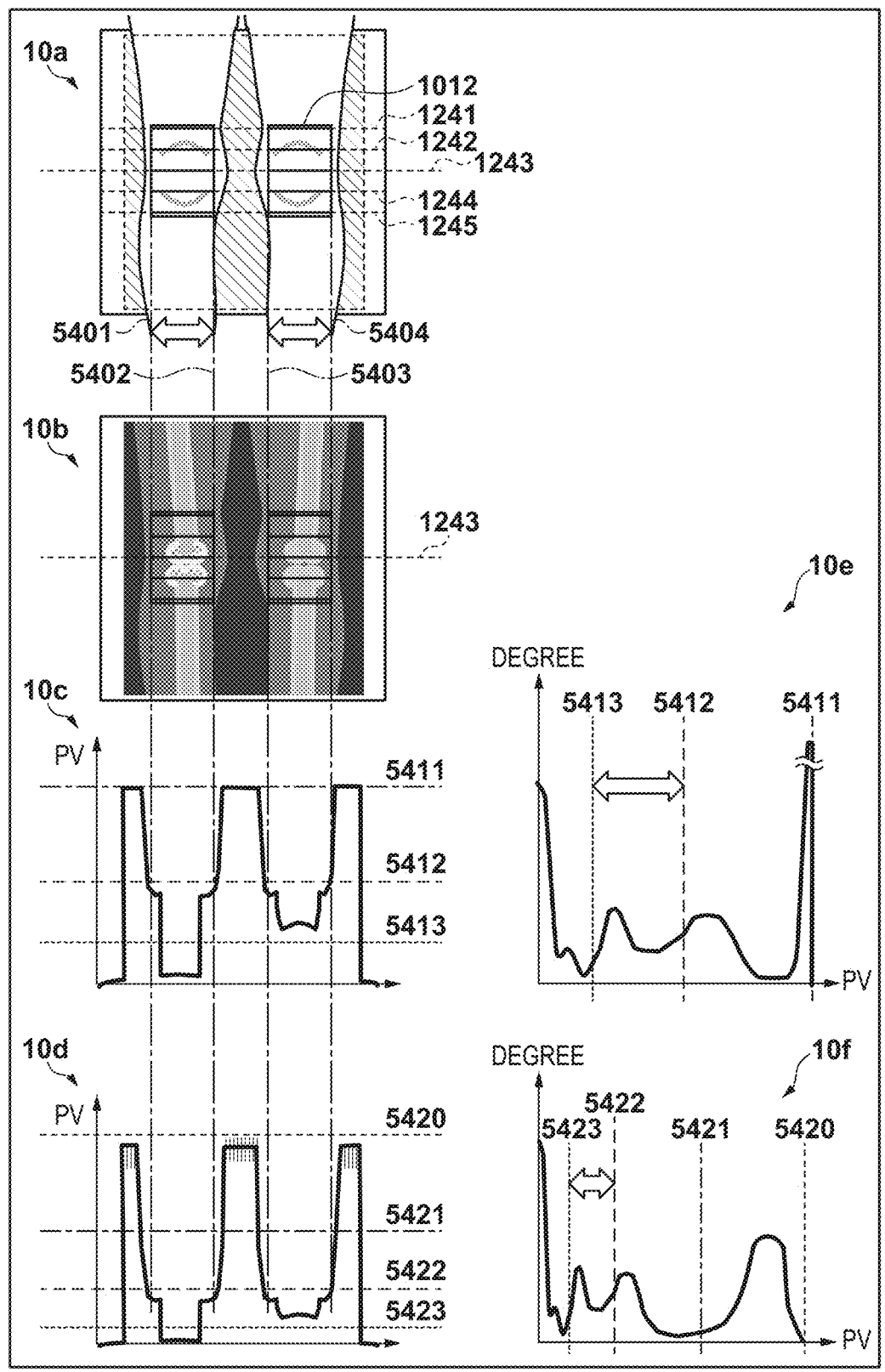
FIG. 10 is a diagram illustrating mid-irradiation adjustment in the method for calculating the dose indicator value.

FIG. 9 is a diagram illustrating the pre-irradiation adjustment of the calculation method for the dose indicator value, and FIG. 10 is a diagram illustrating mid-irradiation adjustment of the calculation method for the dose indicator value. The adjustment processing in FIGS. 9 and 10 and the specific processing in the flow of the present embodiment, illustrated in FIG. 8, will be described below. Although the dose indicator value EI is used as a dose indicator in the present embodiment, a similar technique can be applied to dose indicators in general.

Before radiation imaging, the imaging control apparatus 1002 can specify the region of interest using at least one of (i) a radiation projection region calculated based on position measurement information between the radiation source 1003 and the radiation imaging apparatus 1001, (ii) an optical image of an object in the radiation projection region, obtained by a camera, or (iii) a radiation image of the object captured previously.

FIGS. 9 and 10 illustrate, as an example, a case where the operator obtains a radiation image of both knees of the object. The operator positions the object on a table (not shown) placed between the radiation source 1003 and the radiation imaging apparatus 1001. As indicated by 9a in FIG. 9, an image 5310 (an optical image) is displayed in the display unit 1006 as a real-time video camera image of visible light or infrared light corresponding to the area the radiation image of the object to be captured (the radiation projection region). A two-dimensional outline 5301 of the radiation imaging apparatus 1001, a radiation projection region 5302, and a direct ray region 5303 are shown in the image 5310.

The simplest way to realize this display is simply to perform a real-time display with display light, which indicates the radiation irradiation area, lit, which is a common function of a collimator (not shown) in the radiation source 1003. In this case, the outline 5301 is a two-dimensional outline shape of the table-top radiation imaging apparatus 1001 or a two-dimensional outline shape of the radiation imaging apparatus 1001 under a top panel of the table made of a material that transmits visible light, such as an acrylic material.

In 9b in FIG. 9, a default of five receptor fields 1012 (AEC receptor fields) are displayed in an overlaid manner, in addition to 9a in FIG. 9. When shooting the knee, the default five receptor fields 1012 do not focus on the knee joints which are to be shot and are therefore not appropriate. Thus, for example, the operator makes an instruction to change the position of the receptor fields 1012 (AEC receptor fields) to match the positions of the knee joints, as indicated by 9c in FIG. 9. Furthermore, if the operator is aware in advance that a metal has been inserted into the knee joint on the left side when facing FIG. 9, they can make an instruction to exclude the left knee joint area from the receptor fields 1012 (AEC receptor fields) during shooting.

Alternatively, as indicated by 9*d* in FIG. 9, an overlay display of past images shot in the past can be overlaid in a semi-transparent manner on top of the image indicated by 9*c* in FIG. 9 or the like to clearly indicate the status of the treatment area that was treated in the past. In 9*c* in FIG. 9, it is also possible to use display control to display a status, such as the position of a treatment area such as metal inserted in the knee joint, in an easy-to-understand manner using hatching or coloring of the treatment area such as metal, as indicated by a metal region 5304 in 9*d* in FIG. 9. Similar to the previously recognized case, the operator makes an instruction to exclude the left knee joint area from the receptor fields 1012 (the AEC receptor fields) at the time of shooting as necessary, and makes a change instruction such that the positions of the receptor fields 1012 match the positions of the knee joints.

The capturing of an image of the knee joint illustrates in FIG. 9 is an example, and the receptor fields 1012, which are the operating regions of the dose detection pixels 121, after the processing of "removing the outside of the irradiation area" (S801), "direct ray equivalent region removal" (S802), and "removal of unnecessary areas such as metals" (S803). By calculating the dose indicator value EI of the captured image using the image capturing pixels 101 near the dose detection pixels 121 illustrated in FIG. 6 as the dose indicator value EI and the region information of the set receptor fields 1012, the dose can be managed more accurately than in the past.

With respect to reference to the past images for observing progress, as described above, the operator can use the past images more actively to determine the receptor fields 1012 (AEC receptor fields) rather than simply displaying the images as reference images for determining the receptor fields 1012 (AEC receptor fields). For example, if the receptor fields 1012 (AEC receptor fields) of the referenced past images were originally determined through the same sequence as that described in the present embodiment, the receptor fields 1012 (AEC receptor fields) used when capturing a target past image may be read out using information from the time of shooting, recorded in a given region of a DICOM header by the manufacturer, and displayed as default recommended receptor fields for the receptor fields 1012 (AEC receptor fields) used in the current shooting. Alternatively, it is also possible to derive the appropriate receptor fields 1012 by processing the past images in a similar manner as the method used here, excluding the direct ray region 5303 and the metal region 5304 and calculating the dose indicator value EI. In this process, the recommended shape of the appropriate receptor fields 1012 for the current shooting may be derived, for example. When displaying the recommended receptor fields to the operator, the receptor fields 1012 considered to be in appropriate positions for the image 5310 may be displayed after recognizing the image 5310 and the outline in advance.

Another method for determining the receptor field according to the flowchart in FIG. 8 will be described here. For example, when the radiation imaging apparatus 1001 is disposed in a table or the like, the distance (FDD) between the focal point of the radiation source 1003 and the center of the radiation imaging apparatus 1001, and the positional relationship therebetween, are measured automatically. A collimator aperture is measured by the function of the collimator (not shown) of the radiation source 1003. These measurements can be performed, for example, based on position measurement information of a table and tube holding mechanism, or in a holding mechanism of a tube, which is the radiation source 1003, and the radiation imaging apparatus 1001, provided with an automatic positioning function that enables general imaging. The imaging control apparatus 1002 can obtain this measured information via the aforementioned high-voltage generation apparatus 1004 or the like, and can calculate the outline 5301 and the radiation projection region 5302 based on this information.

Alternatively, the imaging control apparatus 1002 can hold the outline 5301 and the radiation projection region 5302 as information by performing image recognition from a real-time video image. Here, the optical axis, focal point, and image formation point are approximately optically identical to the projection system of the display light from the collimator, the actual radiation irradiation system, and the real-time video camera image capturing optical system, which makes it possible to obtain an accurate outline 5301 and radiation projection region 5302.

Although unlikely to be a problem in cases such as shooting knee joints as illustrated in FIG. 9, the burden on the object due to the continuous projection of visible light may increase when shooting the head area of the like. Accordingly, in addition to the visible light optical system, it is preferable to provide a real-time image capturing system projection system and receiver system using near-infrared light, and an infrared light receiver system used simply as a thermal distribution image capturing system.

Based on this information, the imaging control apparatus 1002 can also perform display control for overlaying the outline 5301 and the radiation projection region 5302 on the real-time video camera image. This makes it possible to perform the process of removing the outside of the irradiation area in step S801 of FIG. 8 before capturing an image.

A method for deriving the direct ray region 5303 will be described next. The calculations can be performed by extracting an image from a real-time video image. To improve the accuracy, a color which is easy to distinguish, and especially a color to which video cameras are highly sensitive, may be used for a top panel (not shown) or the radiation imaging apparatus 1001, or a difference in temperature of the top panel or the radiation imaging apparatus 1001 from the object may be distinguished by using an infrared real-time video camera. It is also possible to extract the direct ray region 5303 from the image 5310 (an optical image) by using an area resembling a sample image for which direct rays have been determined in advance using captured site information and information on past images, by using the threshold information of the fixed threshold method or the p-tile method for region discrimination, and the like. It is useful for the imaging control apparatus 1002 to be capable of calculating percentage information of the direct rays for both the entirety of a dose detection pixel 121 region, described later and illustrated in FIG. 10, and in units of detection lines, sending the calculated information to the radiation imaging apparatus 1001 immediately before radiation imaging, and excluding the direct ray region 5303 accurately based on an integrated value for comparison with AEC threshold computation.

The imaging control apparatus 1002 can perform display control to display an optical image in the display unit 1006 corresponding to the radiation projection region where the radiation image is captured, and the imaging control apparatus 1002 can further perform display control to display, in the display unit 1006, an image in which a radiation image of the object captured in the past is superimposed on the optical image.

Based on this information, the imaging control apparatus 1002 can also perform display control for overlaying the direct ray region 5303 on the real-time video camera image. This makes it possible to perform the process of direct ray equivalent region removal in step S802 of FIG. 8 before capturing an image. As a result, the region within the irradiation area and outside a direct ray-equivalent region can be automatically derived as the equivalent of the remaining receptor fields 1012. Furthermore, it is also possible to identify the receptor fields 1012 as the region of interest based on a receptor field template based on the captured site information of the object. For example, in the case of FIG. 9, it has been determined that the object is "both knees", and thus the area for calculating the dose indicator value EI (the extraction area) can be automatically selected from inside a region which is within the irradiation area and outside the direct ray-equivalent area, centering on the part that can be recognized as the knees.

Here, the processing of the removal of unnecessary areas such as metals before performing radiation imaging of the knee joint, as illustrated in FIG. 9, is mainly performed after information based on object information is transmitted to the radiation imaging apparatus 1001. However, it is possible to perform the removal of unnecessary areas such as metals based on past images of the same object. The imaging control apparatus 1002 can superimpose the past image on the aforementioned image 5310 (the optical image), and can notify the radiation imaging apparatus 1001 that the region excluding the metal region from the area equivalent to the receptor fields 1012, extracted from the image 5310 (the optical image), is used as the receptor fields 1012 in the area for calculating the dose indicator value EI (the extraction area).

With respect to the sequence described with reference to FIG. 9, changes in the shooting site, changes regarding the relative position with respect to the shooting, and the like are completed by time t3, before the operation switch 46 is operated. After the operator instructs the irradiation of radiation by operating the operation switch 46, the imaging control apparatus 1002 and the high-voltage generation apparatus 1004 do not accept any changes in the shooting site, in the relative position with respect to shooting, and the like. After time t3, the receptor fields 1012 in the area for calculating the dose indicator value EI (the extraction area) are finalized, and the imaging control apparatus 1002 notifies the radiation imaging apparatus 1001 of the finalized receptor fields 1012.

Although the foregoing has described an embodiment in which the receptor fields 1012 (the AEC receptor fields) are set in a limited region within the irradiation area and within the object area, as described with reference to FIG. 6 and FIG. 4, it is also possible to set the entire area within the irradiation area and the object area as the receptor field 1012 (AEC receptor fields). In this case, the cycle for determining when the AEC threshold is reached becomes longer as the number of rows of the dose detection pixels 121 to be read out in the receptor fields 1012 (AEC receptor fields) increases. This is therefore not suitable for cases where irradiation time is expected to be within a few milliseconds.

Next, operations performed mainly during the period from time t3 to t7 in FIG. 7 will be described next with reference to FIG. 10. Based on the information of the receptor fields 1012 (AEC receptor fields) of which the radiation imaging apparatus 1001 is notified after time t3, the control circuit 225 determines the dose detection pixels 121 used for the AEC dose calculation this time, from among the dose detection pixels 121 distributed within the image capturing region 100.

As indicated by 10*a* in FIG. 10, five drive lines 1241 to 1245, which correspond to the receptor fields 1012, are selected. As indicated by 10*b* in FIG. 10, the receptor fields 1012 (AEC receptor fields) and the five drive lines 1241 to 1245 selected within the receptor fields 1012 are displayed superimposed on the radiation image to be captured. The other dose detection pixels 121 not selected this time are not driven at all during the radiation irradiation period to shorten the AEC response time and to use the pixels as normal pixels in the image.

By time t5, the drive for correction of the corresponding five dose detection pixels 121 is complete, and the control circuit 225 outputs the irradiation and readout able signal at time t5, and at the same time starts driving for the purpose of AEC dose measurement. In this case, drive signals may be sequentially output to the five drive lines 124 (AEC drive lines) to drive as five rows, or the five drive lines may be selected simultaneously to drive as one row. The time required for readout when driving as five rows is five times longer than the time required for readout when driving as one row, but because the spatial resolution is increased, the determination for each line area can be made in detail, as will be described later. On the other hand, when driving as one row, the time is as fast as ⅕ and the signal components can be secured five times faster, which provides excellent short-time response; however, the spatial resolution is inferior to that of driving as five rows, and thus the accuracy may decrease when performing the integration while inserting fine line area processing. The control circuit 225 can control the driving to vary the number of lines to be driven during shooting, such as driving five rows of drive lines together at the start of radiation irradiation and then driving several rows together after a predetermined time has passed.

When radiation irradiation starts at time t6, outputs corresponding to each of the drive lines 124 (AEC drive lines) are output from the readout circuit 222C (an AEC readout circuit).

10*c* and 10*e* in FIG. 10 indicate a line graph and a histogram of a final image linear to the dose before post-processing in the part corresponding to a drive line 1243 (AEC drive line). 10*d* and 10*f* in FIG. 10 indicate an output waveform and a histogram of one sampling of the drive line 1243 (AEC drive line). Here, in 10*c* and 10*e* of FIG. 10, reference sign 5411 indicates a maximum value of the pixel values; reference sign 5412 indicates a maximum value of a pixel value PV used when calculating the integrated DOSE; and reference sign 5413 indicates a level corresponding to a pixel value corresponding to a minimum value. In 10*d* and 10*f* of FIG. 10, reference sign 5420 indicates the maximum value of the pixel values of the dose detection pixels 121 in one row; reference sign 5421 indicates a pixel value corresponding to reference sign 5411, which is the maximum value in the final image; reference sign 5422 indicates the maximum value of the pixel value PV used when calculating the integrated DOSE; and reference sign 5423 indicates a pixel value level corresponding to a minimum value.

There are several methods for determining the target pixels when calculating the integrated DOSE in the present embodiment. The simplest method is to integrate all of the outputs of pixels corresponding to the dose detection pixels 121 in the area determined by the imaging control apparatus 1002, as determined by the descriptions given previously with reference to FIG. 9. For example, this method integrates all of the outputs of the pixels corresponding to the corrected dose detection pixels 121 between reference signs 5401 and 5402 and between reference signs 5403 and 5404 in 10a in FIG. 10. As described earlier with reference to FIG. 9, the region between reference signs 5401 and 5402 has metal embedded and may therefore be excluded from the integration.

Furthermore, the maximum value 5412 and the minimum value 5413 of the pixel value PV can be determined in advance by referring to past images, as indicated by 10c in FIG. 10, and the integration processing can be performed by excluding these from the integration target within the previously indicated region. In this case, the maximum value 5412 can prevent the radiation dose in the region of interest from reaching the AEC threshold with an underdose when the direct rays in the direct ray region 5303 are intermixed unintentionally, contrary to the instructions from the imaging control apparatus 1002, due to positional skew between the object and the radiation imaging apparatus 1001 or the like. The minimum value 5413 can similarly suppress the effects of irradiation outside the irradiation area or in the metal region, and suppress a situation where the AEC threshold is reached at an overdose of radiation in the region of interest. The dose detection pixels 121 excluded are treated as if they were originally excluded, and the integrated DOSE is calculated to appropriately correspond to the dose per unit of area by normalizing only the dose detection pixels 121 used for the integration.

In actuality, it is difficult to determine the pixel values of 10d in FIG. 10 by sampling every time from 10c in FIG. 10. This is because how much of the dose is irradiated at each sampling time is not set. Therefore, the maximum value 5412, the minimum value 5413, and the like are determined by a ratio to the direct ray region. Furthermore, because the radiation doses that reach are of course different between 10c in FIGS. 10 and 10d in FIG. 10, the pixel value 5420 (the maximum value of the pixel value; 10d in FIG. 10) in the direct ray dose region in the output waveform of instance of sampling is difference from the pixel value 5411 in the direct ray region of the final image (the maximum value of the pixel value; 10c in FIG. 10). Therefore, to determine the maximum value 5422 of the pixel value PV and the pixel value level 5423 corresponding to the minimum value in the output waveform of one instance of sampling before irradiation, the pixel value 5420 of the direct ray region is calculated by the imaging control apparatus 1002 from the setting information of the radiation generation apparatus immediately before the start of irradiation, and is communicated to the radiation imaging apparatus 1001.

Another method for obtaining the maximum value 5422 of the pixel value PV and the pixel value level 5423 corresponding to the minimum value is to prepare a memory that holds integration results for each line graph pixel indicated by 10d in FIG. 10, and perform the integration computations based on an addition or addition-averaged line graph updated after each instance of sampling. This is done while calculating the histogram of the line graph (10f in FIG. 10). If the arithmetic processing can be completed in time, the calculation result may be obtained for each sampling cycle, or, because line graph-like integration results are held, the histogram may be calculated every several line cycles.

Because the imaging control apparatus 1002 knows the percentage of the direct ray region calculated from a camera image or the like in advance, it is possible to calculate the maximum value 5422 from the histogram in 10f in FIG. 10 using the direct ray region information as the threshold information in the p-tile method. Similarly, the imaging control apparatus 1002 can calculate the minimum value 5423 from the histogram in 10f in FIG. 10 by obtaining the percentage of metal parts by referring to non-irradiated areas, past images, and the like. From these, it is possible to determine the range of pixel values of the dose detection pixels 121 that should be converted for comparison with the AEC threshold during irradiation. The advantage of using a histogram is that it is not necessary to know the absolute values of the pixel values in the direct ray part, and even if the direct ray part is saturated, the previous maximum value 5422 can be derived if the ratio of the direct ray area to the other areas is known.

Next, processing performed when the position information of the subject prior to imaging irradiation, i.e., the receptor fields 1012 determined in advance, and the area actually to be irradiated with radiation are misaligned will be described with reference to FIG. 11. Consider a case where the right foot was supposed to be in the state indicated by 11a in FIGS. 11 and 11b in FIG. 11, but in reality the right foot was shifted rightward as indicated by 11c in FIGS. 11 and 11d in FIG. 11. Possible causes of such misalignment include an object which is moving, or misalignment between the optical axis of the camera and the optical axis of the radiation, and the like.

Figure 11:
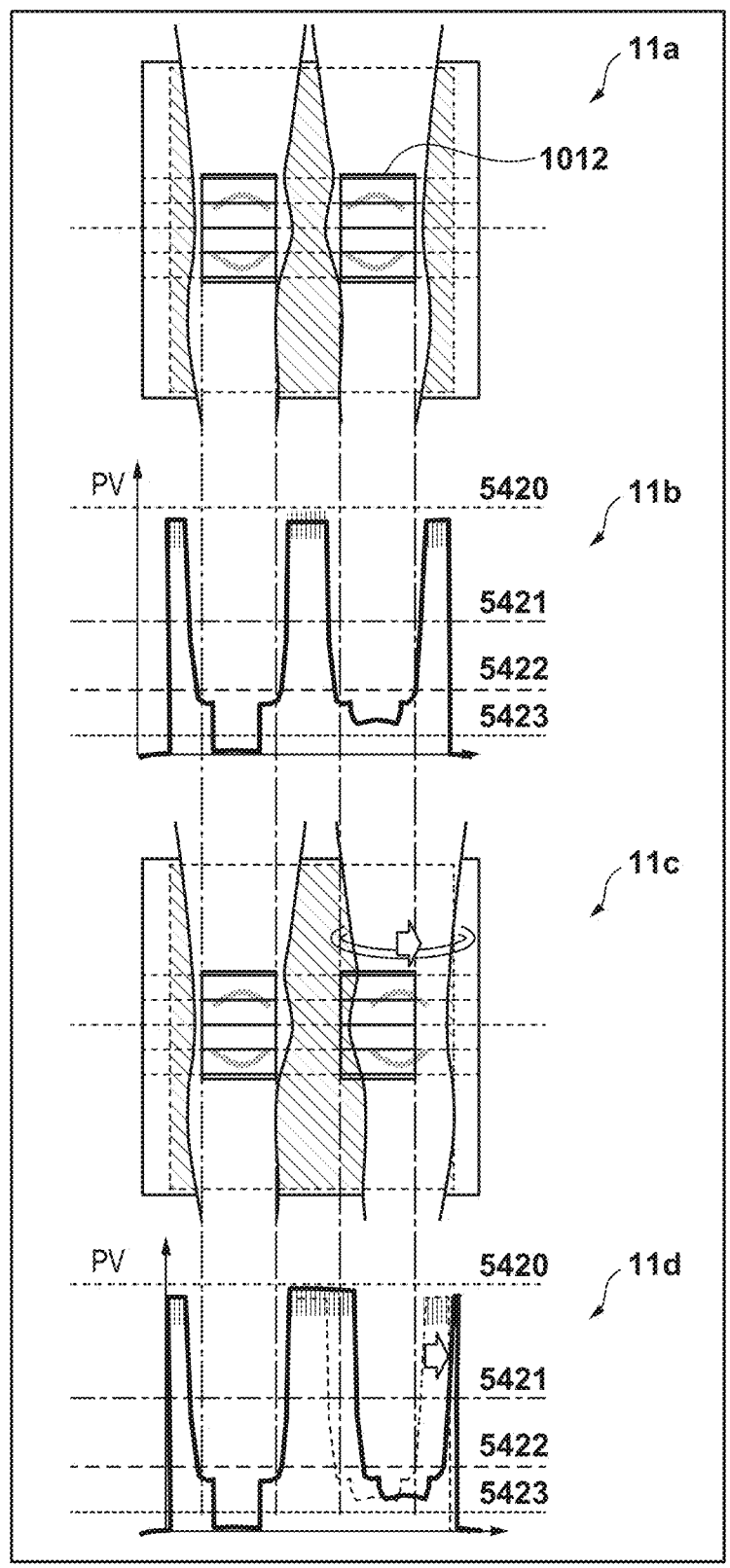
FIG. 11 is a diagram illustrating processing performed when a receptor field determined in advance and an area of radiation in actual irradiation are misaligned.

If the entire area of the receptor fields 1012 is simply integrated as indicated by 11d in FIG. 11, the direct ray region 5303 will be present within the area of the receptor fields 1012, and thus the AEC threshold will be reached with an insufficient dose in the region of interest. An under-irradiated images may be shot, resulting in a decrease in grain quality, and in some cases, the need to shoot the image again.

The method described with reference to FIG. 10 prevents the AEC threshold from being reached with insufficient irradiation. In other words, if the maximum value 5422 can be obtained by determining the region of direct rays in advance using a video camera image or the like, even if direct rays unexpectedly enter the receptor fields 1012, the direct rays can be excluded from the region to be integrated, which enables comparison with the AEC threshold with almost no loss of accuracy. Similarly, by obtaining the ratio of the region outside the irradiation area from the video camera image or collimator information in advance, a minimum value equivalent to the minimum value 5423 can be obtained. This makes it possible to ensure that information outside the irradiation area does not affect the comparison operation between the AEC threshold and the integrated value, even if the receptor fields 1012 are not set in advance. In other words, the integrated value may be obtained only from the results of the dose detection pixels 121 between the maximum value 5422 and the minimum value 5423, and compared with the AEC threshold. This method is particularly effective for shooting conditions where the ratio of the direct rays to the object does not change significantly even if the position of the object moves slightly, such as when the object is small relative to the irradiation area.

As described earlier, the threshold reached signal is output from the radiation imaging apparatus 1001, and radiation irradiation is stopped at the appropriate timing. The radiation image is then transferred to the imaging control apparatus 1002, and the equivalent of the integrated DOSE value compared to the actual AEC threshold is also transferred to the imaging control apparatus 1002. The imaging control apparatus 1002 re-calculates the dose indicator value EI from the obtained radiation image using the dose indicator value EI calculation algorithm, compares the dose target value EIt set as the AEC threshold, the dose indicator value EI calculated from the image, and the integrated DOSE value corresponding to when the AEC threshold is exceeded, and calculates the respective differences, and particularly, the dose target value EIt, the dose indicator value EI, and the deviation DI. It is also possible to derive conversion coefficients for setting the AEC threshold from the dose target value EIt such that the deviation DI between the dose target value EIt and the dose indicator value EI is minimized through machine learning of those deviations or the like, and to provide feedback for setting the AEC threshold.

It is possible to reduce the deviation DI by having the imaging control apparatus 1002 associate the part of the radiation image where the dose target value EIt corresponds to the dose detection pixels 121 in the receptor fields 1012 of the radiation image. Additionally, the imaging control apparatus 1002 can perform display control for displaying, in the display unit 1006 in an identifiable manner, a location, in the region of interest, that corresponds to a dose target value set as the threshold. Then, the imaging control apparatus 1002 performs display control such as hatching or coloring to make the part corresponding to the dose target value EIt in the receptor fields 1012 and the location of the dose detection pixels 121 identifiable, and displays this in the display unit 1006, which also improves the usability for the operator.

According to the embodiments, doses can be managed appropriately by reducing deviation between a dose target value set as a radiation irradiation threshold and a dose indicator value from when an image is actually taken.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging system comprising a radiation imaging apparatus and an imaging control apparatus, the radiation imaging apparatus including a dose detection pixel that detects a dose of radiation irradiated from a radiation source, and the imaging control apparatus controlling the radiation imaging apparatus, wherein before radiation imaging, the imaging control apparatus:
   specifies a position of the dose detection pixel in a region of interest for calculating a dose indicator value of a radiation image, determines a threshold according to the position of the dose detection pixel, and transmits the position of the dose detection pixel and the threshold to the radiation imaging apparatus,
   the radiation imaging apparatus:
   makes a setting of the position of the dose detection pixel in the region of interest and the threshold transmitted from the imaging control apparatus, and performs imaging based on the setting, and
   the imaging control apparatus:
   sets the threshold so that a deviation between the dose indicator value calculated by using pixel value of the radiation image and a dose target value determined as the threshold is reduced.

2. The radiation imaging system according to claim 1, wherein before radiation imaging, the imaging control apparatus specifies the region of interest using at least one of (i) a radiation projection region calculated based on position measurement information between the radiation source and the radiation imaging apparatus, (ii) an optical image of an object in the radiation projection region, obtained by a camera, or (iii) a radiation image of the object captured previously.

3. The radiation imaging system according to claim 2, wherein the imaging control apparatus further specifies the region of interest based on a template, the template being based on captured site information of the object.

4. The radiation imaging system according to claim 2, wherein the imaging control apparatus performs display control for displaying the optical image in a display in correspondence with the radiation projection region in which the radiation image is captured.

5. The radiation imaging system according to claim 4, wherein the imaging control apparatus further performs display control for displaying, in the display, an image in which the radiation image of the object captured previously is superimposed on the optical image.

6. The radiation imaging system according to claim 2, wherein the imaging control apparatus performs display control for displaying, in the display in an identifiable manner, a location, in the region of interest, that corresponds to a dose target value set as the threshold.

7. The radiation imaging system according to claim 1, wherein the imaging control apparatus controls irradiation from the radiation source such that the dose target value set as the threshold and the dose indicator value in the radiation image become equal.

8. The radiation imaging system according to claim 1, wherein based on a signal read out from a correction pixel from which visible light is shielded, the radiation imaging apparatus corrects a signal read out from the dose detection pixel in the region of interest specified by the imaging control apparatus, and calculates an integrated dose of the radiation based on the signal corrected.

9. The radiation imaging system according to claim 8, further comprising a radiation generation controller that controls the radiation source to stop irradiating the radiation when the integrated dose of the radiation that reaches the radiation imaging apparatus exceeds a threshold.

10. The radiation imaging system according to claim 1, wherein the radiation imaging apparatus includes an image capturing pixel for generating the radiation image.

11. The radiation imaging system according to claim 1, wherein the imaging control apparatus:
  identifies the position of the dose detection pixel in the region of interest by removing an area included in a radiation image of an object that is unnecessary for calculating the dose indicator value from an optical image of the object in a radiation projection region, and
  determines the threshold according to the position of the dose detection pixel, and
  transmits the position of the dose detection pixel and the threshold to the radiation imaging apparatus.

12. An imaging control apparatus comprising a dose detection pixel that detects a dose of radiation irradiated from a radiation source, the imaging control apparatus making a setting of a position of the dose detection pixel in a region of interest which is transmitted and a threshold, and controlling a radiation imaging apparatus to capture an image based on the setting, wherein
  before radiation imaging, the imaging control apparatus:
  specifies a position of the dose detection pixel in a region of interest for calculating a dose indicator value of a radiation image, determines a threshold according to the position of the dose detection pixel, and transmits the position of the dose detection pixel and the threshold to the radiation imaging apparatus, and
  the imaging control apparatus:
  sets the threshold so that a deviation between the dose indicator value calculated by using pixel value of the radiation image and a dose target value determined as the threshold is reduced.

13. The imaging control apparatus according to claim 12, wherein before radiation imaging, the imaging control apparatus specifies the region of interest using at least one of (i) a radiation projection region calculated based on position measurement information between the radiation source and the radiation imaging apparatus, (ii) an optical image of an object in the radiation projection region, obtained by a camera, or (iii) a radiation image of the object captured previously.

14. The imaging control apparatus according to claim 13, wherein the imaging control apparatus further specifies the region of interest based on a template, the template being based on captured site information of the object.

15. The imaging control apparatus according to claim 13, wherein the imaging control apparatus performs display control for displaying the optical image in a display in correspondence with the radiation projection region in which the radiation image is captured.

16. The imaging control apparatus according to claim 15, wherein the imaging control apparatus further performs display control for displaying, in the display, an image in which the radiation image of the object captured previously is superimposed on the optical image.

17. The imaging control apparatus according to claim 12, wherein the imaging control apparatus performs display control for displaying, in the display in an identifiable manner, a location, in the region of interest, that corresponds to the dose target value set as the threshold.

18. The imaging control apparatus according to claim 12, wherein the imaging control apparatus controls irradiation from the radiation source such that the dose target value set as the threshold and the dose indicator value in the radiation image become equal.

19. A radiation imaging method of a radiation imaging apparatus comprising a dose detection pixel that detects a dose of radiation irradiated from a radiation source, the radiation imaging method comprising:
  setting a radiation imaging apparatus before radiation imaging based on information transmitted from an imaging control apparatus,
  wherein before the radiation imaging, the imaging control apparatus specifies a position of the dose detection pixel in a region of interest for calculating a dose indicator value of a radiation image, determines a threshold according to the position of the dose detection pixel, and transmits the position of the dose detection pixel and the threshold to the radiation imaging apparatus,
  in the setting step, a setting of the position of the dose detection pixel in the region of interest and the threshold transmitted from the imaging control apparatus is made, and imaging is performed based on the setting, and
  in a control step, the threshold is set so that a deviation between the dose indicator value calculated by using pixel value of the radiation image and a dose target value determined as the threshold is reduced.

20. A non-transitory computer readable storage medium storing a program that causes a computer to execute the radiation imaging method according to claim 19.

\* \* \* \* \*